United States Patent
Dibra et al.

(10) Patent No.: US 11,842,437 B2
(45) Date of Patent: Dec. 12, 2023

(54) MARKER-LESS AUGMENTED REALITY SYSTEM FOR MAMMOPLASTY PRE-VISUALIZATION

(71) Applicant: Arbrea Labs AG, Zurich (CH)

(72) Inventors: Endri Dibra, Zurich (CH); Niko Benjamin Huber, Zurich (CH)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 17/204,503

(22) Filed: Mar. 17, 2021

(65) Prior Publication Data

US 2021/0201565 A1 Jul. 1, 2021

Related U.S. Application Data

(63) Continuation-in-part of application No. PCT/CH2019/050022, filed on Sep. 19, 2019.

(Continued)

(51) Int. Cl.
*G06T 17/00* (2006.01)
*G06T 17/20* (2006.01)
(Continued)

(52) U.S. Cl.
CPC .............. *G06T 17/00* (2013.01); *A61B 34/10* (2016.02); *A61B 90/361* (2016.02); *A61B 90/37* (2016.02);
(Continued)

(58) Field of Classification Search
CPC ..... G06T 15/205; G06T 17/20; G06T 7/0012; G06T 2200/24; G06T 2207/20084;
(Continued)

(56) References Cited

U.S. PATENT DOCUMENTS 5,975,893 A 11/1999 Chishti et al.
6,227,850 B1 5/2001 Chishti et al.
(Continued)

OTHER PUBLICATIONS

Bogo et al., Keep It SMPL: Automatic Estimation of 3D Human Pose and Shape from a Singe Image, Sep. 16, 2016, pp. 561-578, International Conference on Financial Cryptography and Data Security; [Lecture Notes in Computer Science; Lect. Notes Computer], Springer, Berlin, Heidelberg.

(Continued)

*Primary Examiner* — Michelle Chin
(74) *Attorney, Agent, or Firm* — Lowenstein Sandler LLP

(57) ABSTRACT

A medical image might be generated for a patient image using a convolutional neural network trained on prior patient pre-procedure and post-procedure 2D images. A method might generate 3D models from pre-procedure 2D images and from post-procedure 2 images, and train the convolutional neural network with training images being the 3D models, to generate at least one 3D model of the present patient from the 2D image of the present patient, apply the 3D model of the present patient to the convolutional neural network in an inference stage, and apply patient-specific parameters derived from the proposed surgical procedure as a second input to the convolutional neural network in the inference stage to generate an inferred post-surgery 3D model of the present patient given the patient-specific parameters.

22 Claims, 12 Drawing Sheets

Related U.S. Application Data

(60) Provisional application No. 62/733,508, filed on Sep. 19, 2018.

(51) Int. Cl.

| | | |
|---|---|---|
| *G06T 15/20* | (2011.01) | |
| *G06T 7/00* | (2017.01) | |
| *G06N 3/08* | (2023.01) | |
| *G06N 3/04* | (2023.01) | |
| *G16H 50/70* | (2018.01) | |
| *G16H 50/50* | (2018.01) | |
| *G16H 30/40* | (2018.01) | |
| *G16H 30/20* | (2018.01) | |
| *G16H 20/40* | (2018.01) | |
| *A61B 90/00* | (2016.01) | |
| *A61B 3/10* | (2006.01) | |
| *A61B 34/10* | (2016.01) | |
| *G06F 18/214* | (2023.01) | |
| *A61B 17/00* | (2006.01) | |

(52) U.S. Cl.
CPC ............ *G06F 18/214* (2023.01); *G06N 3/04* (2013.01); *G06N 3/08* (2013.01); *G06T 7/0012* (2013.01); *G06T 15/205* (2013.01); *G06T 17/20* (2013.01); *G16H 20/40* (2018.01); *G16H 30/20* (2018.01); *G16H 30/40* (2018.01); *G16H 50/50* (2018.01); *G16H 50/70* (2018.01); *A61B 2017/00796* (2013.01); *A61B 2034/104* (2016.02); *A61B 2034/105* (2016.02); *A61B 2090/363* (2016.02); *A61B 2090/367* (2016.02); *A61B 2090/373* (2016.02); *G06T 2200/24* (2013.01); *G06T 2207/20084* (2013.01); *G06T 2207/30068* (2013.01); *G06T 2210/41* (2013.01)

(58) Field of Classification Search
CPC ....... G06T 2210/41; G06T 17/00; G06N 3/08; G06K 9/6256; A61B 34/10
See application file for complete search history.

(56) References Cited

U.S. PATENT DOCUMENTS

| | | |
|---|---|---|
| 6,227,851 B1 | 5/2001 | Chishti et al. |
| 6,299,440 B1 | 10/2001 | Phan et al. |
| 6,318,994 B1 | 11/2001 | Chishti et al. |
| 6,371,761 B1 | 4/2002 | Cheang et al. |
| 6,386,878 B1 | 5/2002 | Pavlovskaia et al. |
| 6,406,292 B1 | 6/2002 | Chishti et al. |
| 6,409,504 B1 | 6/2002 | Jones et al. |
| 6,457,972 B1 | 10/2002 | Chishti et al. |
| 6,488,499 B1 | 12/2002 | Miller |
| 6,514,074 B1 | 2/2003 | Chishti et al. |
| 6,554,611 B2 | 4/2003 | Chishti et al. |
| 6,582,229 B1 | 6/2003 | Miller et al. |
| 6,602,070 B2 | 8/2003 | Miller et al. |
| 6,621,491 B1 | 9/2003 | Baumrind et al. |
| 6,688,886 B2 | 2/2004 | Hughes et al. |
| 6,726,478 B1 | 4/2004 | Isiderio et al. |
| 6,729,876 B2 | 5/2004 | Chishti et al. |
| 6,739,869 B1 | 5/2004 | Taub et al. |
| 6,767,208 B2 | 7/2004 | Kaza |
| 6,783,360 B2 | 8/2004 | Chishti |
| 7,040,896 B2 | 5/2006 | Pavlovskaia et al. |
| 7,063,532 B1 | 6/2006 | Jones et al. |
| 7,074,038 B1 | 7/2006 | Miller |
| 7,074,039 B2 | 7/2006 | Kopelman et al. |
| 7,077,647 B2 | 7/2006 | Choi et al. |
| 7,108,508 B2 | 9/2006 | Hedge et al. |
| 7,134,874 B2 | 11/2006 | Chishti et al. |
| 7,156,661 B2 | 1/2007 | Choi et al. |
| 7,160,107 B2 | 1/2007 | Kopelman et al. |
| 7,241,142 B2 | 7/2007 | Abolfathi et al. |
| 7,293,988 B2 | 11/2007 | Wen |
| 7,309,230 B2 | 12/2007 | Wen |
| 7,357,634 B2 | 4/2008 | Knopp |
| 7,555,403 B2 | 6/2009 | Kopelman et al. |
| 7,637,740 B2 | 12/2009 | Knopp |
| 7,689,398 B2 | 3/2010 | Cheng et al. |
| 7,736,147 B2 | 6/2010 | Kaza et al. |
| 7,746,339 B2 | 6/2010 | Matov et al. |
| 7,783,099 B1 | 8/2010 | Stefan et al. |
| 7,844,356 B2 | 11/2010 | Matov et al. |
| 7,844,429 B2 | 11/2010 | Matov et al. |
| 7,865,259 B2 | 1/2011 | Kuo et al. |
| 7,878,804 B2 | 2/2011 | Korytov et al. |
| 7,880,751 B2 | 2/2011 | Kuo et al. |
| 7,904,308 B2 | 3/2011 | Arnone et al. |
| 7,930,189 B2 | 4/2011 | Kuo |
| 7,942,672 B2 | 5/2011 | Kuo |
| 7,970,627 B2 | 6/2011 | Kuo et al. |
| 7,970,628 B2 | 6/2011 | Kuo et al. |
| 8,038,444 B2 | 10/2011 | Kitching et al. |
| 8,044,954 B2 | 10/2011 | Kitching et al. |
| 8,075,306 B2 | 12/2011 | Kitching et al. |
| 3,092,215 A1 | 1/2012 | Stone-Collonge et al. |
| 8,099,268 B2 | 1/2012 | Kitching et al. |
| 8,108,189 B2 | 1/2012 | Chelnokov et al. |
| 3,126,726 A1 | 2/2012 | Matov et al. |
| 8,260,591 B2 | 9/2012 | Kass et al. |
| 8,275,180 B2 | 9/2012 | Kuo |
| 8,401,826 B2 | 3/2013 | Cheng et al. |
| 8,439,672 B2 | 5/2013 | Matov et al. |
| 8,562,338 B2 | 10/2013 | Kitching et al. |
| 8,591,225 B2 | 11/2013 | Wu et al. |
| 8,788,285 B2 | 7/2014 | Kuo |
| 8,843,381 B2 | 9/2014 | Kuo et al. |
| 8,874,452 B2 | 10/2014 | Kuo |
| 8,896,592 B2 | 11/2014 | Boltunov et al. |
| 8,930,219 B2 | 1/2015 | Trosien et al. |
| 9,037,439 B2 | 5/2015 | Kuo et al. |
| 9,060,829 B2 | 6/2015 | Sterental et al. |
| 9,125,709 B2 | 9/2015 | Matty |
| 9,211,166 B2 | 12/2015 | Kuo et al. |
| 9,220,580 B2 | 12/2015 | Borovinskih et al. |
| 9,364,296 B2 | 6/2016 | Kuo |
| 9,375,300 B2 | 6/2016 | Matov et al. |
| 9,414,897 B2 | 8/2016 | Wu et al. |
| 9,492,245 B2 | 11/2016 | Sherwood et al. |
| 9,569,736 B1 * | 2/2017 | Ghesu .................. G06N 20/00 |
| 9,642,678 B2 | 5/2017 | Kuo |
| 9,786,084 B1 * | 10/2017 | Bhat ...................... G06T 15/04 |
| 10,248,883 B2 | 4/2019 | Borovinskih et al. |
| 10,342,638 B2 | 7/2019 | Kitching et al. |
| 10,463,452 B2 | 11/2019 | Matov et al. |
| 10,595,966 B2 | 3/2020 | Carrier, Jr. et al. |
| 10,617,489 B2 | 4/2020 | Grove et al. |
| 10,722,328 B2 | 7/2020 | Velazquez et al. |
| 10,758,322 B2 | 9/2020 | Pokotilov et al. |
| 10,779,718 B2 | 9/2020 | Meyer et al. |
| 10,792,127 B2 | 10/2020 | Kopelman et al. |
| 10,828,130 B2 | 11/2020 | Pokotilov et al. |
| 10,835,349 B2 | 11/2020 | Cramer et al. |
| 10,973,611 B2 | 4/2021 | Pokotilov et al. |
| 10,996,813 B2 | 5/2021 | Makarenkova et al. |
| 10,997,727 B2 | 5/2021 | Xue et al. |
| 11,020,205 B2 | 6/2021 | Li et al. |
| 11,020,206 B2 | 6/2021 | Shi et al. |
| 11,026,766 B2 | 6/2021 | Chekh et al. |
| 11,033,359 B2 | 6/2021 | Velazquez et al. |
| 11,071,608 B2 | 7/2021 | Derakhshan et al. |
| 11,096,763 B2 | 8/2021 | Akopov et al. |
| 11,116,605 B2 | 9/2021 | Nyukhtikov et al. |
| 11,147,652 B2 | 10/2021 | Mason et al. |
| 11,151,753 B2 | 10/2021 | Gao et al. |
| 11,154,381 B2 | 10/2021 | Roschin et al. |
| 11,259,896 B2 | 3/2022 | Matov et al. |
| 11,357,598 B2 | 6/2022 | Cramer |
| 11,395,717 B2 | 7/2022 | Yuryev et al. |

(56) References Cited

U.S. PATENT DOCUMENTS

| | | |
|---|---|---|
| 11,432,908 B2 | 9/2022 | Kopelman et al. |
| 11,464,604 B2 | 10/2022 | Makarenkova et al. |
| 11,478,334 B2 | 10/2022 | Matov et al. |
| 11,484,389 B2 | 11/2022 | Sterental et al. |
| 11,521,732 B2 | 12/2022 | Levin et al. |
| 11,534,272 B2 | 12/2022 | Li et al. |
| 11,553,988 B2 | 1/2023 | Mednikov et al. |
| 11,633,268 B2 | 4/2023 | Moalem et al. |
| 11,642,195 B2 | 5/2023 | Gao et al. |
| 11,651,494 B2 | 5/2023 | Brown et al. |
| 11,654,001 B2 | 5/2023 | Roschin et al. |
| 2003/0008259 A1 | 1/2003 | Kuo et al. |
| 2003/0143509 A1 | 7/2003 | Kopelman et al. |
| 2003/0207227 A1 | 11/2003 | Abolfathi |
| 2004/0137400 A1 | 7/2004 | Chishti et al. |
| 2004/0152036 A1 | 8/2004 | Abolfathi |
| 2004/0197728 A1 | 10/2004 | Abolfathi et al. |
| 2004/0259049 A1 | 12/2004 | Kopelman et al. |
| 2005/0182654 A1 | 8/2005 | Abolfathi et al. |
| 2005/0244791 A1 | 11/2005 | Davis et al. |
| 2006/0127836 A1 | 6/2006 | Wen |
| 2006/0127852 A1 | 6/2006 | Wen |
| 2006/0127854 A1 | 6/2006 | Wen |
| 2006/0275731 A1 | 12/2006 | Wen et al. |
| 2006/0275736 A1 | 12/2006 | Wen et al. |
| 2008/0306724 A1 | 12/2008 | Kitching et al. |
| 2010/0009308 A1 | 1/2010 | Wen et al. |
| 2010/0068672 A1 | 3/2010 | Arjomand et al. |
| 2010/0068676 A1 | 3/2010 | Mason et al. |
| 2010/0092907 A1 | 4/2010 | Knopp |
| 2010/0167243 A1 | 7/2010 | Spiridonov et al. |
| 2013/0204599 A1 | 8/2013 | Matov et al. |
| 2016/0005106 A1 | 1/2016 | Giraldez et al. |
| 2016/0310235 A1 | 10/2016 | Derakhshan et al. |
| 2017/0119471 A1 | 5/2017 | Winner et al. |
| 2017/0273760 A1 | 9/2017 | Morton et al. |
| 2018/0260951 A1* | 9/2018 | Yang .................. A61B 6/5217 |
| 2018/0280118 A1 | 10/2018 | Cramer |
| 2019/0035149 A1* | 1/2019 | Chen .................. G06V 40/166 |
| 2019/0213779 A1* | 7/2019 | Sutton .................. G06T 19/00 |
| 2019/0328487 A1 | 10/2019 | Levin et al. |
| 2019/0328488 A1 | 10/2019 | Levin et al. |
| 2020/0155274 A1 | 5/2020 | Pimenov et al. |
| 2020/0297458 A1 | 9/2020 | Roschin et al. |
| 2020/0306011 A1 | 10/2020 | Chekhonin et al. |
| 2020/0306012 A1 | 10/2020 | Roschin et al. |
| 2021/0134436 A1 | 5/2021 | Meyer et al. |
| 2021/0174477 A1 | 6/2021 | Shi et al. |

OTHER PUBLICATIONS

Dibra et al., Monocular RGB Hand Pose Inference from Unsupervised Refinable Nets, Jun. 18, 2018, IEEE/CVF Conference on Computer Vision and Pattern Recognition Workshops (CVPRW).

Dibra et al., Recovery of the 3D Virtual Human: Monocular Estimation of 3D Shape and Pose with Data Driven Priors, May 31, 2018, a dissertation submitted to ETH Zurich.

International Search Report and Written Opinion issued for International Patent Application No. PCT/CH2019/050022, dated Dec. 18, 2109, 21 pages.

Lacher et al., A comparative Study of Breast Surface Reconstruction for Aesthetic Outcome Assessment, Sep. 4, 2017, pp. 514-522, Distributed Computing : 19th International Conference, Disc 2005, Cracow, Poland, Sep. 26-29, 2005. Proceedings; [Lecture Notes in Computer Science], Springer Berlin Heidelberg, Berlin, Heidelberg.

Payer et al., Regressing Heatmaps for Multiple Landmark Localization Using CNNs, Oct. 2, 2016, pp. 230-238, International Conference on Financial Cryptography and Data Security; [Lecture Notes in Computer Science; Lect. Notes Computer], Springer, Berlin, Heidelberg.

Saito et al., Photorealistic Facial Texture Inference Using Deep Neural Networks, Jul. 21, 2017, pp. 2326-2335, IEEE Computer Society Conference on Computer Vision and Pattern Recognition Proceedings, IEEE Computer Society, US.

* cited by examiner (a)

(b)

(c)

MARKER-LESS AUGMENTED REALITY SYSTEM FOR MAMMOPLASTY PRE-VISUALIZATION

CROSS-REFERENCES TO PRIORITY AND RELATED APPLICATIONS

This application is a continuation-in-part of International Patent Application Serial No. PCT/CH2019/050022, filed Sep. 19, 2019, which claims the benefit of and is a non-provisional of U.S. Patent Application Ser. No. 62/733,508 filed on Sep. 19, 2018, entitled "Marker-Less Augmented Reality System for Mammoplasty Pre-Visualization".

The entire disclosures of applications recited above are hereby incorporated by reference, as if set forth in full in this document, for all purposes.

FIELD

The present disclosure generally relates to the use of augmented or mixed reality in visualization of surgical body modifications and more particularly to apparatus and techniques for creating real-time visualizations that are based on two-dimensional body images and computed markers.

BACKGROUND

Surgical procedures for making body modifications, such as cosmetic surgery or reconstructive surgery are complex operations and it is desirable for a patient to understand what their post-operation body would look like. A number of systems are in use, but are complicated, costly to operate, and require considerable setup.

A common example is mammoplasty for breast reconstruction or cosmetic surgery. Having a visualization of the post-operation body would help the patients and allow for in-depth discussions with the surgeon regarding options and outcomes. Mammoplasty might be used for breast augmentation, reduction, reconstruction, to address asymmetry or changes due to weight gain, weight loss or pregnancy, of following breast cancer treatments. Thus, there could be a variety of reasons for mammoplasty and one consideration is the final look or shape of the breasts. Other body-modifying surgeries are also known and there the final look or shape can be a consideration.

Uncertainty as to what the patient's breasts would look like after the surgery can result in unmet or unrealistic expectations from either the patient or the surgeon and this can lead to dissatisfaction and potential re-makings that are costly. Approximately 20% of breast augmentation surgeries result in re-makings, to a big extent due to unmet expectations in terms of size or style.

One conventional approach to the visualization problem is to show a patient numerous photographs of "before and after" examples from prior patients and hope to find an acceptable example. Another approach is to use expensive equipment that captures three-dimensional ("3D") imagery from the patient, perhaps in a clinical setting, and perhaps allows for 3D manipulations of renderings of the patient's upper body torso. Yet another conventional approach uses an expensive 3D scanner that captures data and renders a 3D model offline for later manipulation.

More recently, there have been attempts at real-time demonstration of before and after surgery situations that require placement of tracking markers or fiducials onto the patient's body, on elastic bands covering the breasts, manual skin tone selection, etc. for the virtual breasts. These bands might cause distortion, must be fitted properly, and may not work.

Some approaches require depth sensors attached to specialized devices, which can be cumbersome outside of a clinical setting. These factors can limit their use by patients in their own homes.

SUMMARY

A computational device for generating a medical image relative to a present patient, from possibly limited information and possibly overcoming a lack of tracking marker data, the device might comprise a first storage for a first plurality of two-dimensional (2D) images, comprising images of prior patients before respective surgical procedures, a second storage for a second plurality of 2D images, comprising images of the prior patients after their respective surgical procedures, a camera for capturing at least one 2D image of the present patient, a convolutional neural network, and a computational module. The computational module might (a) generate a first plurality of three-dimensional (3D) models from the first plurality of 2D images, (b) generate a second plurality of 3D models from the second plurality of 2D images, (c) train the convolutional neural network with training images being 3D models from the first plurality of 3D models and a first ground truth for the input 3D model is a post-surgery 3D model from the second plurality of 3D models, wherein the input 3D model and the post-surgery 3D model are derived from the same prior patient of the prior patients, (d) generate at least one 3D model of the present patient from the at least one 2D image of the present patient, (e) apply the at least one 3D model of the present patient as a first input to the convolutional neural network in an inference stage, (f) obtain patient-specific parameters corresponding to a proposed surgical procedure, and (g) apply the patient-specific parameters derived from the proposed surgical procedure as a second input to the convolutional neural network in the inference stage to generate an inferred post-surgery 3D model of the present patient given the patient-specific parameters. A display might be provided to display a view of the inferred post-surgery 3D model. The view of the inferred post-surgery 3D model might comprise at least one 2D view of the inferred post-surgery 3D model of the present patient. A breast model fitting might be based on tracking points and differentiable renderers. Skin appearance might be a third input to the convolutional neural network and the convolutional neural network might be configured to derive a parametrization of the skin appearance model.

The first image of the first plurality of 2D images might be a synthetically generated image set, and the computational device further might comprise program code for: (a) generating a first set of semantic landmarks in images of the first plurality of 2D images, (b) obtaining the second plurality of 2D images, wherein the second plurality of 2D images includes instances of sampled body parts of persons other than the present patient and corresponding to a user body part depicted in the at least one 2D image of the present patient, wherein at least a second image of the second plurality of 2D images and a third image of the second plurality of 2D images have different photographic parameters, (c) obtaining a second set of semantic landmarks in images of the second plurality of 2D images, (d) training a first convolutional neural network (CNN) with inputs of the first plurality of 2D images and the second plurality of 2D images with a second ground truth of the first set of semantic landmarks and the second set of semantic landmarks, wherein training is to train the first CNN to form a first trained CNN to output one or more output semantic landmarks related to an input image without requiring a ground truth of the input image, (e) generating, using the first trained CNN with the at least one 2D image of the present patient as a CNN input, a third set of semantic landmarks representing landmarks of the user body part, (f) obtaining a mesh model for the second plurality of 2D images, wherein the mesh model corresponds to a 3D instance model, of the instances of the sampled body parts of the persons other than the present patient, (g) generating, from the mesh model and the third set of semantic landmarks, a user body part mesh, wherein the user body part mesh is an approximation of a 3D user body part model, of the user body part depicted in the at least one 2D image of the present patient, (h) obtaining a target body part mesh, distinct from the user body part mesh, and (i) generating a modified view image, of the user body part, modified to reflect differences between the target body part mesh and the user body part mesh while retaining at least some texture of the user body part from the at least one 2D image of the present patient.

The first set of semantic landmarks in the images of the first plurality of 2D images might be obtained by projecting 3D vertices from sources for generating the first plurality of 2D images from synthetic mesh parts onto the first plurality of 2D images.

A method of generating a medical image relative to a present patient might comprise obtaining a first plurality of two-dimensional (2D) images of prior patients before respective surgical procedures, generating a first plurality of three-dimensional (3D) models from the first plurality of 2D images, obtaining a second plurality of 2D images of the prior patients after their respective surgical procedures, generating a second plurality of 3D models from the second plurality of 2D images, training a convolutional neural network, wherein a training image for the convolutional neural network is an input 3D model from the first plurality of 3D models and a first ground truth for the input 3D model is a post-surgery 3D model from the second plurality of 3D models, wherein the input 3D model and the post-surgery 3D model are derived from the same prior patient of the prior patients, obtaining at least one 2D image of the present patient, generating at least one 3D model of the present patient from the at least one 2D image of the present patient, applying the at least one 3D model of the present patient as a first input to the convolutional neural network in an inference stage, obtaining patient-specific parameters corresponding to a proposed surgical procedure, applying the patient-specific parameters derived from the proposed surgical procedure as a second input to the convolutional neural network in the inference stage, and outputting, from the convolutional neural network, an inferred post-surgery 3D model of the present patient given the patient-specific parameters.

The method might further comprise generating a first image of the first plurality of 2D images synthetically, generating a first set of semantic landmarks in images of the first plurality of 2D images, obtaining the second plurality of 2D images, wherein the second plurality of 2D images includes instances of sampled body parts of persons other than the present patient and corresponding to a present patient body part depicted in the at least one 2D image of the present patient, wherein at least a second image of the second plurality of 2D images and a third image of the second plurality of 2D images have different photographic parameters, obtaining a second set of semantic landmarks in images of the second plurality of 2D images, training a first convolutional neural network (CNN) with inputs of the first plurality of 2D images and the second plurality of 2D images with a second ground truth of the first set of semantic landmarks and the second set of semantic landmarks, wherein training is to train the first CNN to form a first trained CNN to output one or more output semantic landmarks related to an input image without requiring a ground truth of the input image, generating, using the first trained CNN with the at least one 2D image of the present patient as a CNN input, a third set of semantic landmarks representing landmarks of the present patient body part, obtaining a mesh model for the second plurality of 2D images, wherein the mesh model corresponds to a first 3D model of the instances of the sampled body parts of the persons other than the present patient, generating, from the mesh model and the third set of semantic landmarks, a user body part mesh, wherein the user body part mesh is an approximation of a second 3D model of the present patient body part, obtaining a target body part mesh, distinct from the user body part mesh, generating a modified view image, of the present patient body part, modified to reflect differences between the target body part mesh and the user body part mesh while retaining at least some texture of the present patient body part from the at least one 2D image of the present patient.

The different photographic parameters might comprise one or more of lighting conditions under which a given image was captured, albedo conditions under which the given image was captured, and/or camera parameters with which the given image was captured.

The first set of semantic landmarks in the images of the first plurality of 2D images might be obtained by projecting 3D vertices from sources for generating the first plurality of 2D images from synthetic mesh parts onto the first plurality of 2D images.

The second set of semantic landmarks in the images of the second plurality of 2D images might be obtained by aligning displacements of obtained landmarks that are output from the first trained CNN having as input the second plurality of 2D images. The mesh model for the second plurality of 2D images might be generated using a silhouette contour.

The user body part mesh might be approximated using differentiable rendering and might comprise displaying the modified view image, of the present patient body part, in an augmented reality apparatus.

The modified view image might comprise a rendering of a 3D augmented-reality model that visually combines a first view of the first 3D model and a second view of a third 3D model of a post-surgery example body shape. The 3D augmented-reality model might included mapping of portions of the first 3D model of the present patient to portions of the third 3D model of the post-surgery example body shape. Generating the user body part mesh might comprise generating the user body part mesh from one or more of a morphable mesh, a parametric mesh model, or a parametric model.

A method of generating a modified view image, of a user body part of a user, from a user input image depicting the user body part, might comprise generating a first set of images might comprise a first plurality of two-dimensional images from the first set of images, generating a first set of semantic landmarks in images of the first set of images, training a first convolutional neural network (CNN) with inputs of the first set of images with a first ground truth of the first set of semantic landmarks, wherein training is to train the first CNN to form a first trained CNN to output one or more output semantic landmarks related to an input image without requiring a ground truth of the input image, obtaining the user input image depicting the user body part, generating, using the first trained CNN with the user input image as a CNN input, a second set of semantic landmarks representing landmarks of the user body part, obtaining a mesh model for the first set of images, wherein the mesh model corresponds to a three-dimensional model of instances of sampled body parts of persons other than the user, generating, from the mesh model and the second set of semantic landmarks, a user body part mesh, wherein the user body part mesh is an approximation of a three-dimensional model of the user body part depicted in the user input image, obtaining a target body part mesh, distinct from the user body part mesh, generating the modified view image of the user body part, modified to reflect differences between the target body part mesh and the user body part mesh while retaining at least some texture of the user body part from the user input image.

A computational device might comprise a camera for capturing images of a patient, a computation module for generating a 3D model of the patient from captured images, including images that lack physical markers added to a body of the patient, storage for user preferences, and a display for displaying a rendering of a 3D AR model that is a merger of the 3D model of the patient and a 3D model of post-surgery example body shape. The images might be two-dimensional images. The 3D AR model might be derived from a statistically plausible mesh model learned from captured data. The 3D AR model might include mapping of portions of the 3D model of the patient to portions of the 3D model of the post-surgery example body shape. The computational device might comprise a breast model fitting based on tracking points and differentiable renderers. The computational device might comprise breast model fitting based on an upper torso/breast tracker based on learned features. As used herein, "patient" can refer to a patient who has a scheduled cosmetic surgery, a patient who is considering cosmetic surgery or someone who is merely interested in what the results of surgery might look like whether or not they ever plan to be an actual patient. The body part could be breasts, a stomach, a thigh, legs, a face, a nose, a buttock, or other body part.

The computational device might also include program code to implement and/or perform steps of deriving a skin appearance model. Using the skin appearance model as an input to a convolutional neural network of the computational device, an output dataset might be provided and can result in a higher-quality model using fewer computational resources than other methods. From the output dataset of the convolutional neural network, the computational device can derive a parametrization of the skin appearance model.

The functionality and operations of the computational device might be implemented by software comprising instructions that, when executed by a processor, perform the functions or operations specified. The computational device thus might include a processor, storage for program code instructions, and other elements needed for computation.

This Summary is provided to introduce a selection of concepts in a simplified form that are further described below in the Detailed Description. This Summary is not intended to identify key features or essential features of the claimed subject matter, nor is it intended to limit the scope of the claimed subject matter. A more extensive presentation of features, details, utilities, and advantages of the surface computation method, as defined in the claims, is provided in the following written description of various embodiments of the disclosure and illustrated in the accompanying drawings.

BRIEF DESCRIPTION OF THE DRAWINGS

Various embodiments in accordance with the present disclosure will be described with reference to the drawings, in which.

DETAILED DESCRIPTION

Figure 1:
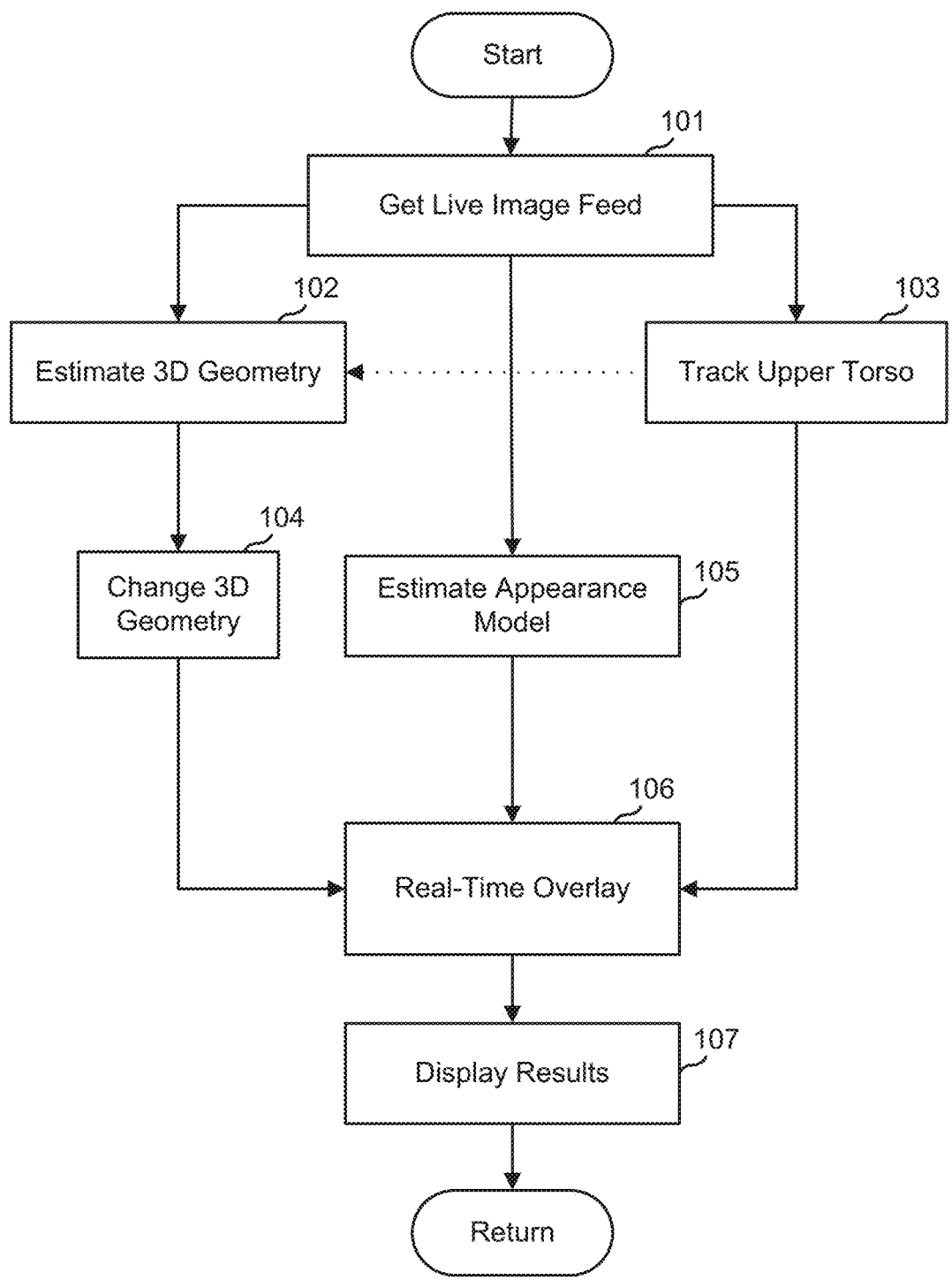
FIG. 1 is a flowchart of elements of a process for obtaining inputs, performing computation, and presenting outputs of an augmented reality solution according to embodiments of the present invention.

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Apparatus and methods are provided herein to present a simple-to-use, real-time visualizer of potential surgical body modifications. While body modifications other than breast surgery are envisioned, many examples are presented using breast surgery as the example, without any intent to limit the disclosure to a specific body modification surgery, unless otherwise specified. A marker-less tool based on augmented and mixed reality might be used for pre-visualization of cosmetic surgery or mammoplasty, for home personal use or a cosmetic surgeon's office or clinic. As used herein, "patient" can refer to a patient who has a scheduled cosmetic surgery, a patient who is considering cosmetic surgery or someone who is merely interested in what the results of surgery might look like whether or not they ever plan to be an actual patient. In the latter case, the person might be using the apparatus and methods described herein with or without any consultation or interaction with doctors or other health professionals, and may just be using the apparatus or methods out of curiosity.

As will be explained below in more detail, an apparatus might comprise an input device for capturing patient images, data and selections, a computational device for generating 3D models and renderings, and an output device for presenting imagery (images, video, etc.) to the patient, surgeon, or other viewer. In some embodiments, the input device, computational device and the output device are the same device, such as a smartphone or an augmented reality apparatus such as augmented reality glasses. In another example, the input device is a smartphone, the computational device is a server to which the smartphone connects, and the output device is a network-connected virtual reality head display.

The apparatus captures two-dimensional ("2D") images of the patient's relevant body parts, obtains metadata about the images, such as lighting and other details, obtains user preferences from the patient, and possibly also body measurements of the patients. From these inputs, the apparatus can generate a usable 3D model of the patient's body portions (the "before" model) and generate a usable 3D model of the patient's body with the proposed surgical modifications shown the "after" model). Generation of the 3D models can be done without requiring tracking markers on the patient's body.

The apparatus can display imagery corresponding to the 3D models. In one approach, the apparatus can display rendered models of the before model, the after model, or augmented reality ("AR") imagery showing the "after" model rendered and aligned with a real-time image of the patient. In the latter case, the model might be adjusted according to the patient's movements as mixed reality ("MR") and with a display that provides the appearance of pass-through viewing.

As used herein, references to AR can be extended to MR unless otherwise indicated. Generally, augmented reality includes presentation of imagery, and possibly also sounds, sometimes in a display that rotates as the viewer's head or view rotates, where the imagery includes synthetic content and real-world content displayed together. In some embodiments, the synthetic content reacts to the real-world content, in real time. For example, in one embodiment, the input is one or more images of the patient's body and the output is those one or more images with a synthetic image overlaid and blended with the original image(s). In another embodiment, the patient might be moving and the synthetic image overlaid and blended is video that tracks and aligns with those movements, as the tracking can be done using computer vision techniques as described herein and analyzing the real scene/movement, the synthetic video is dynamically adjusted based on the movements that were detected. In yet another embodiment, the synthetic video is generated after detecting movement of body parts or objects that would, if the synthetic body parts existed in the space in which they are overlaid, intersect with the synthetic body parts. For example, with this embodiment, a woman could use the apparatus to overlay possible breast modifications, move around relative to the image capture device, and see on the display video wherein the modifications appear in the correct place in the video relative to her body and also the modifications appear to react to her hand pressing on them.

Real-time rendering, processing or presentation of computational results or imagery (e.g., images, video, AR display of renderings, etc.) as used herein refers to the generation in a timely manner such that interactivity can be provided. For example, if a patient has 2D images captured and has to wait 24 hours to see a rendered AR presentation of an "after" model, that would not allow for much interactivity. Real-time might include some small delay, as might be needed for short communication, computation, and display processing, but is quick enough to allow for some patient perception that the apparatus is responding nearly immediately to their inputs.

Different devices might be used. Input collection and output display might be done on one or more of a mobile device, such as a smartphone, tablet, laptop, AR headset, VR goggles, or displayed on stationary devices such as monitors, mirrors, projectors, etc.

In the examples herein, as explained, details may reference breast surgery, but unless otherwise indicated, the teachings could be extended to other body surgery (e.g., face, nose, waist, hips, etc.). Also, some of the uses of the apparatus and methods herein could be applied beyond body surgery to other 3D visualization needs, such as, e.g., virtual clothes fitting.

Examples of platforms include an iOS™ or Android™ app running on a mobile device, e.g., a tablet or phone. Other platforms include a software or web application running on a laptop, a PC, or the like, with the display being the mobile device display, a monitor, a mirror or a projector. The program or application could process the data internally or potentially outside of the mobile device, e.g., on an external PC or utilizing cloud-based processing, in order to maximize performance and realism.

An overview of an example apparatus and method is described below, followed by other detailed examples.

Overview

A session involving data gathering, computation and presentation of augmented reality imagery for the purposes of simulating effects of body surgery or other purposes might involve a smartphone app or program that runs on a portable tablet. An example will be described that uses an app, which is a program that runs on a particular platform. The session might provide for an improved interaction that can provide a marker-less tool based on augmented reality (AR) and mixed reality (MR) for pre-visualization of cosmetic surgery or mammoplasty directly from camera images and without the need of depth sensors.

The app accepts user input, such as details about a patient, such as name, age, height, weight, and surgery plan. The surgery plan might relate to breast reduction, breast enhancement, breast reconstruction, breast adjustment, or other body modification. The inputs might also include parameters for patient selections, preferences and options, such as a value for a target breast size. The input parameters might be obtained by presenting the user (the patient or other user of the device) with sliders to allow the user to slide a slider to a particular value or with form fields to allow the user to enter a value.

The app controls a camera to obtain 2D images of the patient's body, before, after or during the input of the inputs. The camera images might be conventional static images taken with a single lens and represented in data form as RGB images. With the input data and the 2D images, the app can then generate a 3D model of the patient. This might be done on the same device or offloaded to a more powerful processor in a desktop computer or network connected server, such as an Internet-connected server. The 3D model of the patient is the "before" model that represents the patient's current body shape, outline, coloring, etc. and that can be used, if needed, to generate a 3D representation that can be displayed on a display device. One use is to show whether the app is correctly modeling the patient's body, as that model is used for determining the 3D model of the patent after the proposed surgery.

From the 3D before model, the 2D images, and possibly other data, the app determines tracking markers, fiducials, or other reference points on the 3D before model. This might be done using an artificial intelligence engine or a machine learning engine to find the markers from imagery and from detected values for albedo conditions and lighting conditions.

In some embodiments, where artificial intelligence and/or machine learning might benefit, this could be included in the computational process (of the app or elsewhere) that generates the simulated imagery. This might be built using a training set. For example, a separate process might be used to generate meshes derived from captured imagery of bodies of various people in various poses along with alterations of such generated meshes based on learned upper body torso/breast parametric models. Utilizing texture (appearances) from captured imagery and alterations of those, combined with variations in illuminations, camera and object poses, the computational process can include generating a set of realistically looking synthetic data. From that data, fixed 3D points can be generated from that data, such as through sampling mesh vertices. These fixed 3D points can serve as the "marker" points for later use in real-time imagery generation.

The computational process can use a projection operation due to a camera pose and project these 3D points projected onto 2D RGB image points. These created pairs of 2D RGB images and 2D point (virtual marker) positions can be used to train convolutional neural networks or random forest regressors to predict marker points given a new real RGB image at test time. Since the 2D points were generated from the 3D mesh itself, the computational process has available a full correspondence that enables a proper mesh overlay. In order to facilitate this step, and reduce the training data size and search space, the computational process might be programmed to initially train a bounding box detector that constrains the space where the virtual marker tracker is applied. The bounding box detector can also be a CNN trained from pairs of RGB images and bounding box coordinates and size, around the region or interest, and that can also be generated synthetically.

The app might also automatically determine from the inputs and the images what the parameters will be. For example, from a 2D image of the patient, the app might be able to determine where to place control points on the image of the patient to allow the user an interaction portion of the session wherein the patient can select one or more of the controls and move them around to define the desired modifications. With real-time generation of the 3D "after" models and rendering representations of those models, the patient can "dial-in" some modifications and see the effects in real-time.

The app might show the user live imagery of the patient's body and wait to obtain a confirmation from the user, such as a push of a "capture" button to know when to save the imagery for processing and computation.

Following the capture, the app can then generate the 3D "after" model. Then, the app processes the before imagery (what is actually captured) and after imagery (e.g., the simulated, virtual imagery) to generate augmented reality imagery of the "after" body modifications overlaid or blended on the "before" model. In real-time, the augmented reality imagery (or an underlying model that is used to generate imagery) can be updated based on patient movement or input changes, to be able to render realistic imagery of what the body might look like after the proposed surgery.

Each of these can be adjusted for albedo and lighting. The results of this processing can be used to generate a 3D augmented reality model that can be used, perhaps with conventional computer graphics techniques, to generate a representation of the post-surgery body and from that representation, generate imagery (images, video, etc.) showing the post-surgery body possibilities. The imagery can be recorded for later playback, consultations, and the like.

Variations

In some embodiments, dynamics of movement of the 3D augmented reality model are taken into account and computed. For example, a physics engine might be fed parameters about the patient, about muscle and tissue details, as well as the 3D before and after models, and might be able to compute, from those inputs, how elements of the patient's body might move naturally.

In some embodiments, there are an enumerated set of examples, such as particular "looks" to be presented to the patient for selection of options. The app might also include logic to make recommendations among the options. An estimation of the shape can be used for tracking and also for suggesting personalized "after" looks automatically based on data analytics. In some embodiments, the examples include pairs of before and after images from actual past surgeries, including metadata such as size, measurements, and satisfaction levels. Other inputs to the system might include parameterizations of standard beauty surgery principles, where perfect shape models for specific body type/size are created for various sizes of women, and for a specific patient the closest shape to her category is chosen and recommended.

In some embodiments, the app displays predetermined silhouettes and the patient is directed to move into place such that the app shows one of the predetermined silhouettes aligned with the patient's body outline. This can simplify the processing, as motions and positions of the patient in the image are controlled. This also can simplify the fitting and appearance modeling. Making a face analogy, the implementation could be as simple as asking the user to put the face inside a pre-defined circle in the image. The app might present the user with a square, bounding box or a general silhouette and prompt the patient to align their body in the image with the silhouette displayed on the image.

Data Gathering and Overlay

In an example of a data gathering and overlay process, the female patient evaluating breast surgery might sit or stand in front of a camera (possibly integrated in a mobile device) that captures a live video stream of her naked upper body torso. A virtual breast image can be overlaid on the patient's upper body torso, in a marker-less fashion, such that the patient can see live, statically or during motion, her body with virtual breasts correctly and seamlessly placed at the positions of her real ones, with realistic appearance. In the case of motion, the underlying dynamics of the breast is also represented.

3D Model Generation

The virtual breasts might be initially represented from a template mesh, automatically fit to the real upper body torso. The imagery of such virtual breasts are viewed from the patient (potentially together with a surgeon) while being able to turn shoulder-to-shoulder, bend, stretch, move and have wide angle and close-up views of the virtual breasts being consistently displayed over her real ones.

This procedure can run in real time. The resulting 3D models can be used to, in real time, generate images or videos of the modified breasts (from the "after" model) and those can be saved. For secure storage of the data, encryption can be used.

Interestingly, the 3D models can be generated without requiring the placement of markers to track the upper body torso directly from a 2D image. Part of the 3D model generation is the automatic identification of tracking points learned from the images and user input data. The process can use those tracking points in generating the 3D model of the patient (the "before" model), which might include a differentiable rendering iterative step and shape estimation can be utilized to estimate different photographic parameters that capture the appearance model (e.g., albedo, lighting etc.) of the patient.

Utilizing techniques from computer graphics and geometric techniques on 3D meshes, the virtual breasts can be deformed in real-time either through semantic or statistically meaningful sliders or automatically, by a recommendation system suggesting deformations that fit to the underlying body types.

FIG. 1 is a flowchart of elements of a process for obtaining inputs, performing computation, and presenting outputs of an augmented reality solution according to embodiments of the present invention. As illustrated there, a live image feed of the patient and other data is used to generate resulting imagery. In this process, a live image feed from one or more 2D, RGB cameras might be obtained (step 101). Then, a 3D geometry model of the upper body torso and the patient's breasts is obtained through fitting (step 102). A marker-less tracker tracks the body movements in real-time (step 303), and the "before" model based on the real patient texture is obtained (step 105). User input could be obtained to get parameters of the desired modifications (step 104) or they could be automatically generated. These might be generated using a learned recommender system, based on previously captured data or a data structure representing parameters of beauty standards. The 3D before model is modified by the user parameters and preferences.

From the 3D model and the inputs, a realistic virtual overlay of the "after" breasts is generated in real-time (step 106). This overlay is then displayed on mobile or static devices (step 107). This is also illustrated in FIGS. 5 and 7A-7C.

Figure 2:
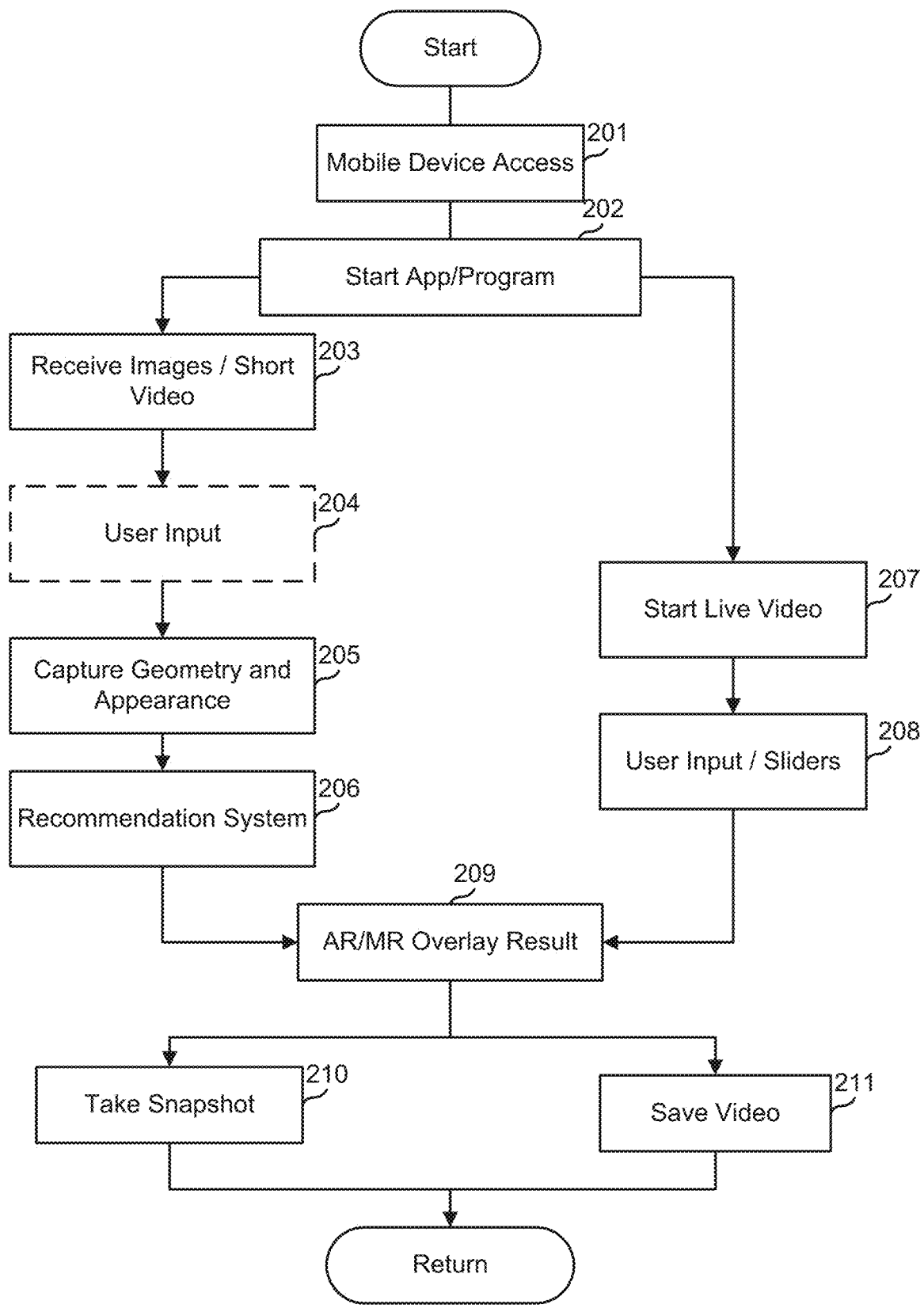
FIG. 2 is a flowchart of elements of a process for handling user input and providing results according to embodiments of the present invention.
Figure 6:
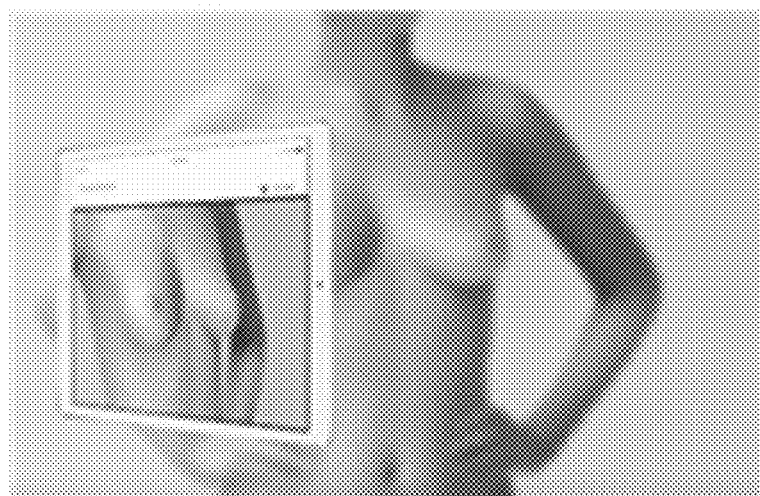
FIG. 6 illustrates examples of 2D image capture and augmented reality presentation according to embodiments of the present invention, taken from different angles and showing three views capturing a subject from a device, that can be used, for example, to reconstruct a body shape and/or track and overlay the new breasts.
Figure 6:
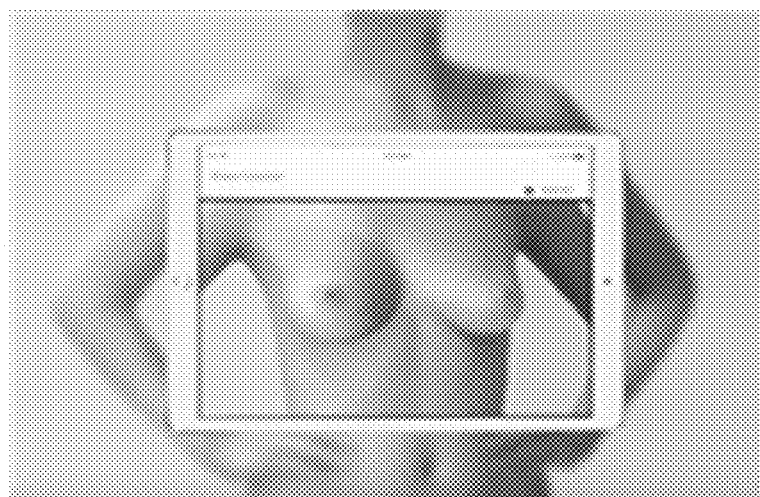
Figure 6:
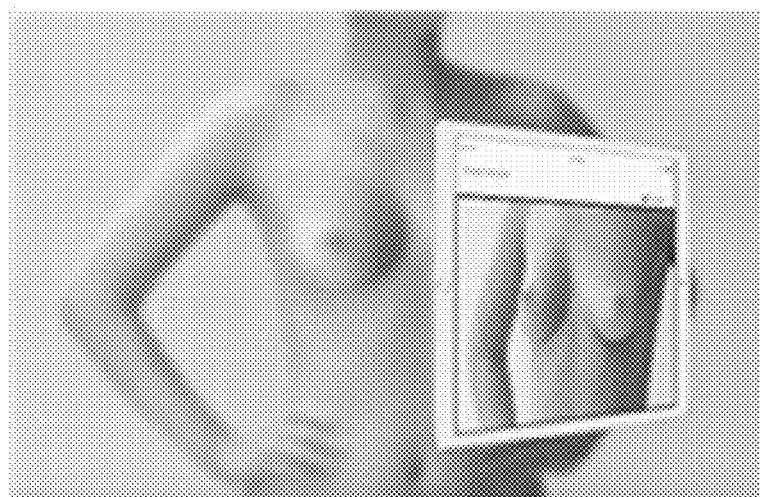

FIG. 2 is a flowchart of elements of a process for handling user input and providing results according to embodiments of the present invention. In this process, a patient may access a mobile device 201, which is either placed somewhere, held by the patient herself or by a second party (which could be a friend or a plastic surgeon). The patient might then start an app 202. Initially, she might make take a couple of pictures of herself in a neutral pose, from various viewing directions with respect to the camera (step 203), etc. (e.g., as shown in FIG. 6). Alternatively, she can provide a short video where she turns from +90 to −90 degrees with respect to the frontal view-point where her naked upper body torso is perpendicular to the device's viewing direction. She can optionally provide patient information, such as her height, known cup size or nipple distance, desired cup size or potentially stay at a certain distance from the camera, where her silhouette roughly matches a pre-defined one (step 204).

As explained above, by prompting the patient to align their body with a displayed silhouette, the app doing the image processing can assume shapes of the patient more easily by restricting the motions and position of the patient in the image. This can simplify the pre-processing and fitting, appearance modeling and also simplify real-time tracking. Based on the face analogy explained above, a silhouette contour is drawn in the image and the user moves with respect to the camera such that most of her body parts, hands, shoulders, upper torso, potentially also head, etc. lie within the predefined contours. This can be an optional step.

At this point, the geometry and appearance capture can take place internally after a patient-triggered signal, e.g., by pressing a button (step 205). From the captured images, the app can estimate her real breast shape, albedo, lighting and potentially camera intrinsic parameters.

The computational processes performed include estimation of her current breast shape, selecting among recommendations that proposes an "after" breast shape (step 206). The patient then, triggers the start of another video where she can realistically visualize her virtual "after" breasts (step 207) derived from the after model. As the video runs, the patient can interactively modify some semantic or statistically learned sliders, or give manual input that can modify the patient inputs and thus change the 3D after model in real time, potentially with texture alterations, e.g., nipple color, scar placement, etc. that are specified by the patient inputs (step 208). What the patient sees in her (potentially projected) device is the desired virtual breast outcome (step 209), correctly placed in the imagery relative to her body location and position and with the AR imagery derived from the after model seamlessly merged with the imagery captured of the patient. This can be saved as images (step 210) or as video (step 211).

Figure 3:
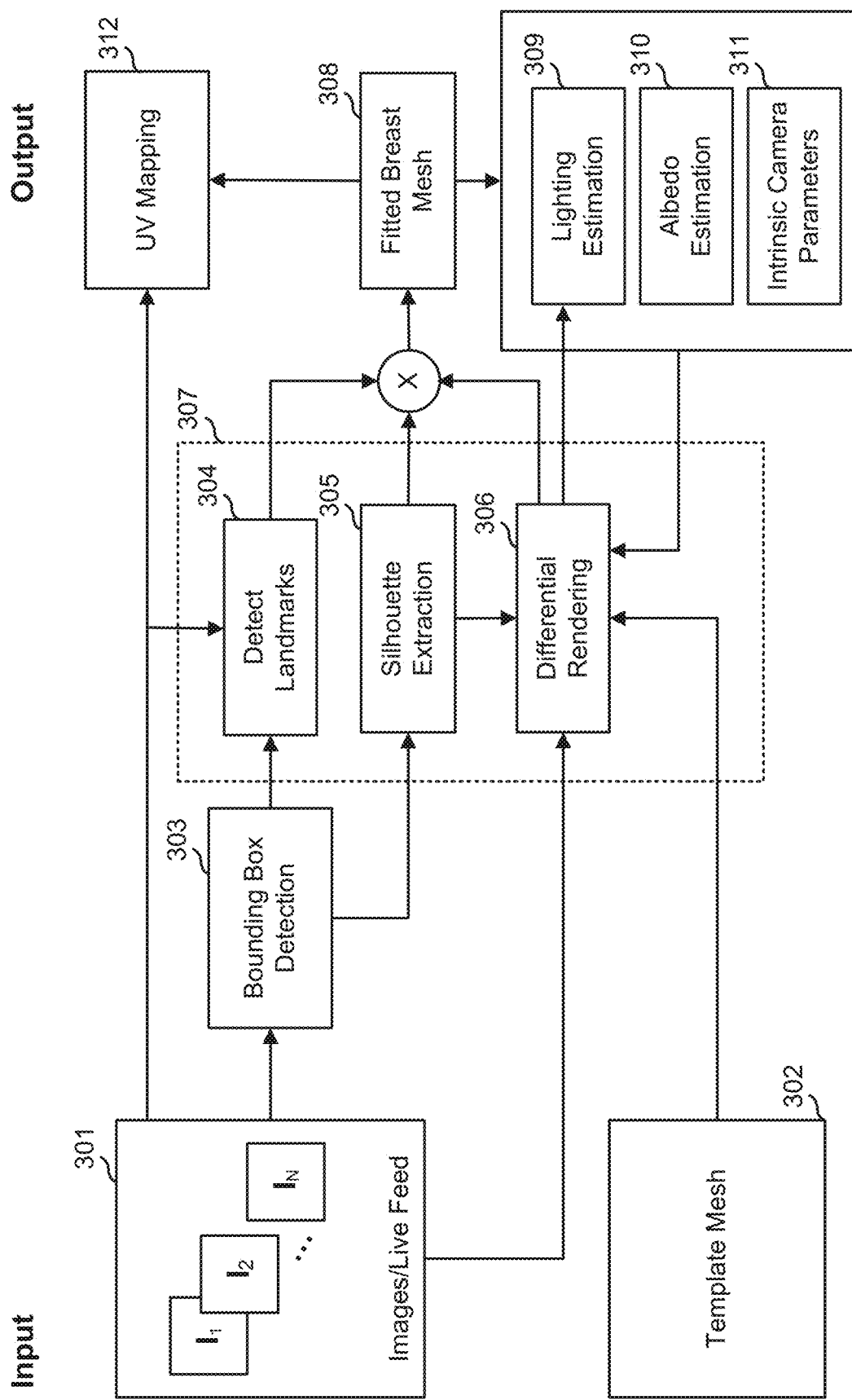
FIG. 3 is a diagram illustrating a process for generating 3D models according to embodiments of the present invention.
Figure 4:
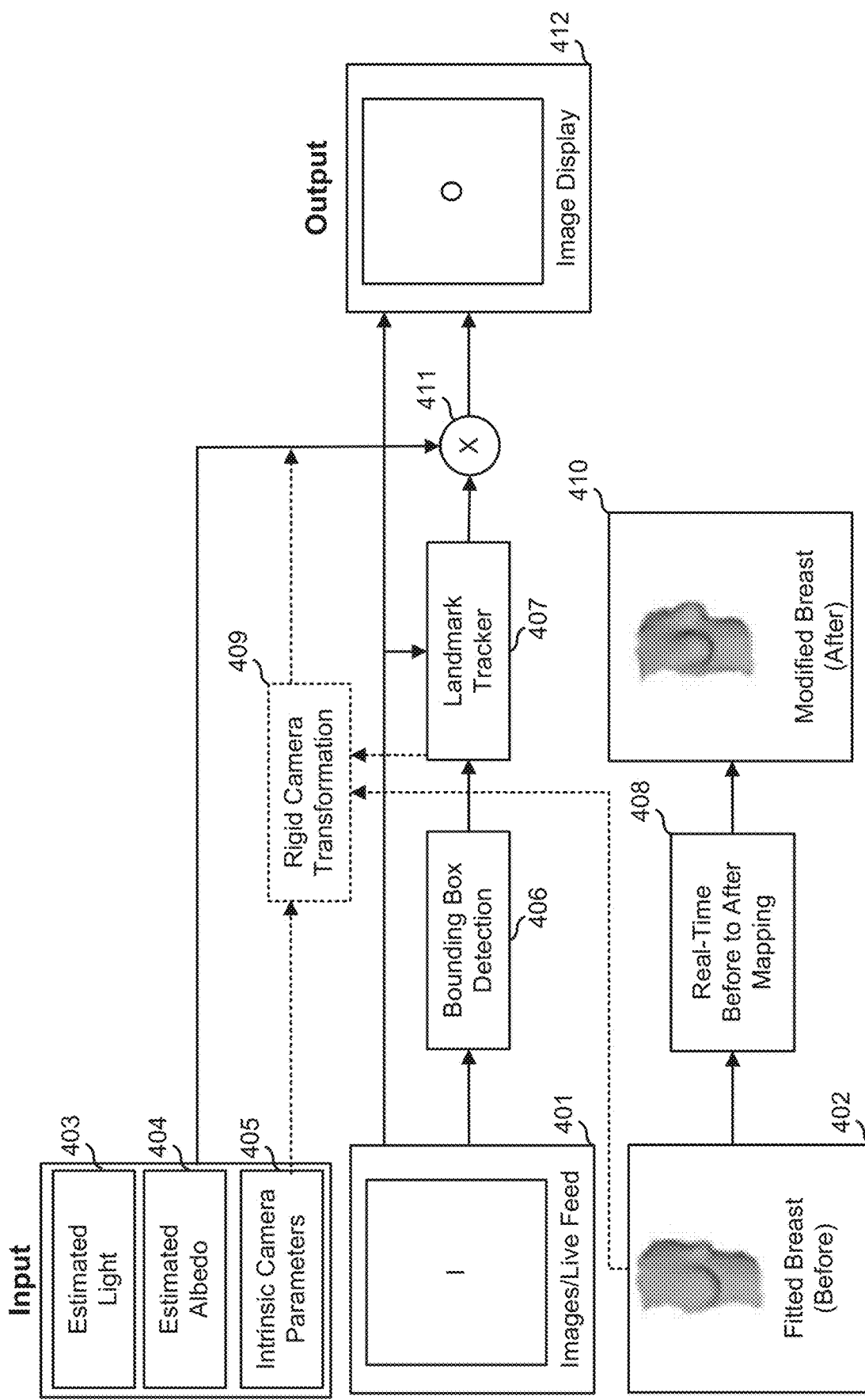
FIG. 4 is a diagram illustrating a computational process for generating augmented reality imagery from inputs using the computational process of FIG. 3 according to embodiments of the present invention.

The pipelines described above can be split in two parts, a geometry and an appearance acquisition component (see FIG. 3) and a tracking and virtual overlay real-time component (see FIG. 4). Then, the personal 3D geometry of the patient's upper body torso and breasts is automatically fit, stemming from an upper torso template mesh (as in FIG. 7B) and utilizing photometric information and learned feature points (as in FIG. 1). This can be achieved either by keeping the patient static and scanning the patient through the camera feed of a movable device (as in FIG. 5), by having various cameras set-up for a multi-view scenario, or by keeping the device static and having the patient slowly turn around camera viewpoint.

FIG. 3 is a diagram illustrating a process for generating 3D models according to embodiments of the present invention. Starting from a short live video feed or a couple of multiple images taken at various timestamps (301), the app first detects a bounding box where the upper body torso lies (303), through a potential combination of CNNs, HOG features and face detectors.

At training time, the app might generate meshes representing bodies of various people in various poses to be captured, along with alterations of such captured meshes based on learned upper body torso/breast parametric models. Utilizing texture (appearances) from captures and alternations of those, combined with variations in illuminations, camera and object poses, the app or other computational process can generate a volume of realistically looking synthetic data.

In addition to the volume of realistically looking synthetic data, the app or other computational process can generate semantic landmarks for body parts in the synthetic data, or obtain those from manual user entry, if necessary. Synthetic images can be generated by first generating synthetic body parts in the form of meshes, which when coupled with synthetic appearance model and lighting conditions, result in the synthetic images. The semantic landmarks for the synthetic images might be obtained from projections of 3D vertices from synthetic mesh parts projected onto the 2D synthetic images.

When combined with images, bounding boxes can be generated that include the breast region or whole upper body. In a specific example, these are pairs of 2D RGB images and bounding box 2D coordinates and size. A bounding box detector can be trained through a CNN to detect bounding boxes from the full image directly. Alternatively, the process can be helped by applying segmentation of the person that can be also a product of a CNN training, where unwanted image parts, walls, other objects are automatically removed. Furthermore, by applying a face detector, the app can restrict the space where the breast bounding box lies. For example, assuming a vertical standing person, the app will process an image with the assumption that it has to always be below the detected face with respect to the y coordinate.

The computational process fits a 3D parametric/template breast mesh (302) into the image defined from the bounding box (307), using a module 304 for detecting landmarks, a module 305 for extracting silhouettes, and a module 306 for performing differentiable rendering. From the results, the app generates a fitted breast mesh texture 308 that is usable for generating the "3D before" model.

In some embodiments, a mapping between points on the fitted breast mesh texture 308 and the "3D before" model are stored as a "UV mapping" dataset. In UV mapping, points from a surface that is modeled in a three-dimensional space (such has where points on the surface have X, Y, and Z coordinates) are mapped to points in a two-dimensional space (which could have U and V coordinates). A simplified dataset might be stored as arrays of mapping points, for example, indicating that a point (Xi, Yi, Zi) in a three-dimensional space and a point (Ui, Vi,) in a two-dimensional space correspond. UV mapping might be useful where there is an image expressed in UV coordinates that is to be textured onto a surface that is expressed in XYZ coordinates.

From the estimated geometry and the initial images, the app can derive a UV mapping 312 between the texture 308 and the mesh. Starting from the fitted mesh, the app uses the differentiable rendering component 306. Assuming a known 3D mesh (the estimated geometry), differentiable rendering attempts to minimize a cost function defined between pixel values depicted in the RGB given image and pixel values produced from a forward rendering process, that considers the mesh, albedo, lighting and camera position. This can be based on a parametric model. One such parametric model uses illumination and the model is minimized iteratively to find an optimum albedo and optimum light coefficient that when used to render the image, best explain the given initial real image.

Other steps include estimating the lighting 309, the albedo 310 and the intrinsic camera parameters 311 directly from the input images 301. Modules 308-312 comprise an output subprocess of this pipeline. The outputs of those modules can be used as inputs to the tracking and virtual overlay pipeline described in FIG. 4.

The bounding box module 303 finds correspondences between 2D pixels depicting the image and 3D positions over a template mesh. The bounding boxes can be generated and trained based on a training procedure such as is explained above. The app can generate these automatically from the inputs and images for estimating the pose of the patient and use this pose to modify the 3D before model in real time. The 2D points and their corresponding 3D ones are initially sampled from the template mesh, utilizing various sampling techniques, such as uniform, blue noise and importance sampling. Other salient points that are discriminative for breast and upper body torso are adopted from the medical literature, e.g., nipple, bust point, inner breast point, etc.

The differentiable rendering module 306 (FIG. 3) can estimate parameters or values for the 3D model geometry, lighting, albedo and camera intrinsic parameters, in an iterative fashion, where, e.g., some parameters are fixed/kept constant and the rest are updated.

FIG. 4 is a diagram illustrating a computational process for generating augmented reality imagery from inputs using the computational process of FIG. 3 according to embodiments of the present invention.

The bounding box around the upper body torso 306 is estimated similar to the geometry capturing step, directly from the incoming camera image, inside which the landmark tracker 304, estimates the 2D points that correspond to the 3D mesh vertices. A rigid camera transformation is obtained (409) from the intrinsic camera parameters 405, the fitted/estimated geometry 402 and the detected landmarks 407. The app obtains the 3D "after" model by modifying the estimated before model (element 402), by a real-time before-to-after mapping component 408. The 3D after model's geometry 410 is combined with the previously estimated appearance model parameters 403 and 404, and can be initially overlaid on the initial imagery with the information coming from the tracked points 407 and extrinsic camera transformation 409. The initial overlay 411, the 3D AR model, is in turn smoothly blended with the texture from the original image 401. This seamless blending can be augmented with in-painting and light enhancing techniques in order to obtain realistic output 412.

The app modifies the 3D AR model with the help of semantically and statistically meaningful parameters set through such as sliders, checkboxes, buttons etc., allowing the patients (or potentially surgeons) to set such parameters interactively. An automatic suggestive system is also proposed with the present invention in order to help both the surgeon and the patient make their decisions. Such a system can be based on machine learning that learns by gathering real datasets of "before" models and "after" models from prior surgeries. In one approach, the app has access to data/scans/images of before and after, along with the body type (tall, short, skinny, obese, etc.) and measurements (shoulder width, hip circumference, etc.), so the app can extract important information/correlations, such as by clustering the data points. A mapping could be learned between classes of body types and "befores" to shapes of "afters", which could be applied to new individuals. Alternatively, the app could create synthetic datasets from plastic surgeon recommendations to simulate and synthesize more data.

The appearance or texture of the individual need not be set by hand, but rather can be determined automatically based on imagery gathered during the fitting process as well as the fitted 3D geometry, through a correct UV mapping estimation between the 2D image and the 2D representation of the 3D model's surface. The app allows texture alterations (e.g., scar placement, etc.) automatically or through manual interaction during the online phase.

In generating the 3D AR model, the app adapts the estimated appearance model and applies it to the modified 3D geometry first and then the combination is overlaid on the 3D before model based on the estimated markers from the landmark tracker 407.

The virtual overlay can be extended with another component which models dynamics of the breast, where the breasts deform and move naturally with respect to a body motion (e.g., jump, jiggle etc.). Dynamics here can be obtained through physically based simulation of fat tissue (potentially with silicon inlay). For performance reasons, a simpler model based on principal components capturing the biggest changing directions that represent shape deformations due to motion can be designed or learned from captured data and transferred to breast shapes of the patients. The tracked feature points, along with other estimated features, e.g., optical flow, enable this step which would improve realism and immersion.

As explained above, extracting the tracking on a new image can be done with careful data generation and training based on CNNs and random forest regressors. With respect to dynamics, assuming a reliable tracking and optical flow components, the app can learn mappings between displacements and learned parameters explaining dynamics.

Figure 5:
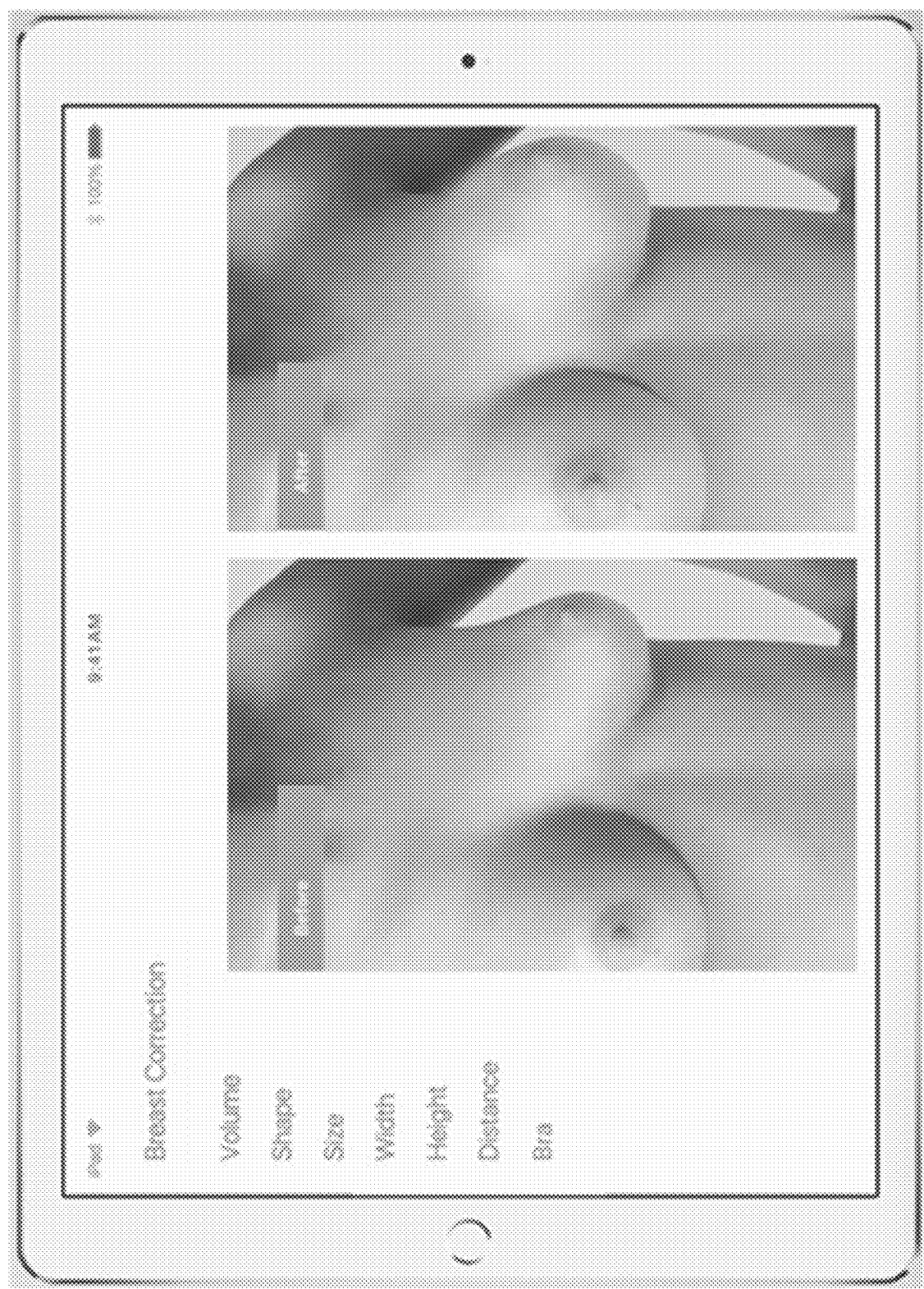
FIG. 5 illustrates an example of a display and user interface for presenting augmented reality imagery based on 3D "before" models and 3D "after" models.

FIG. 5 illustrates an example of a display and user interface for presenting augmented reality imagery based on 3D "before" models and 3D "after" models. Menu items might include inputs for setting parameters for volume, changes in the breast based on given volume, shape changes breast type, size changes the cup size, width changes distance between breasts inner points, height controls lifting, distance changes distance between nipples and bra overlays virtual bras, and other options. These menus can be used to display before and after simultaneously, or could be used to show only the before (real mirror) or after (futuristic mirror).

FIG. 6 illustrates examples of 2D image capture and augmented reality presentation according to embodiments of the present invention, taken from different angles and showing three views capturing a subject from a device, that can be used, for example, to reconstruct a body shape and/or track and overlay the new breasts. In this example, two-dimensional images are captured from three directions.

Figure 7A:
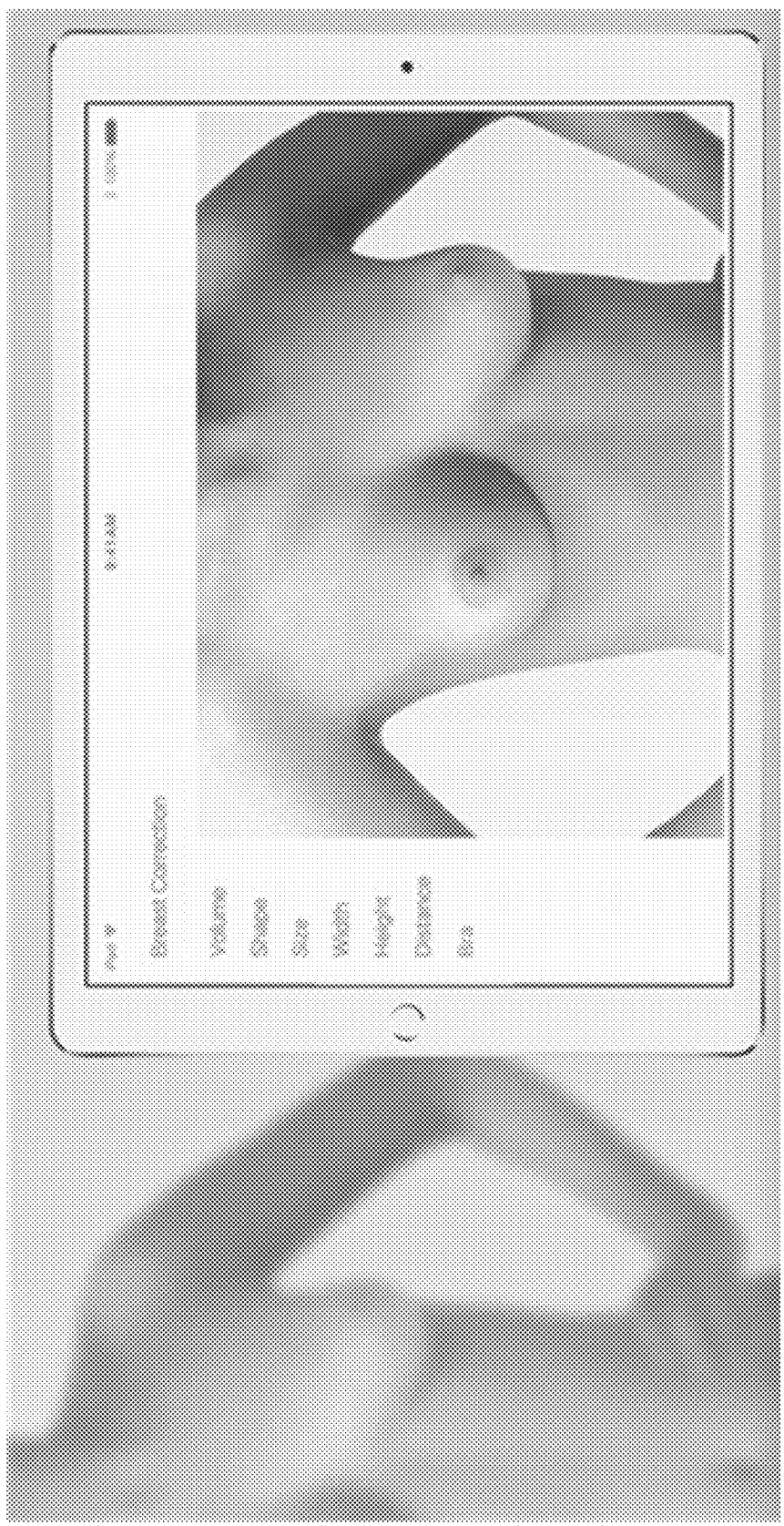
FIGS. 7A, 7B and 7C illustrate three examples of displays of virtual augmentations made to an original breast image.
Figure 7B:
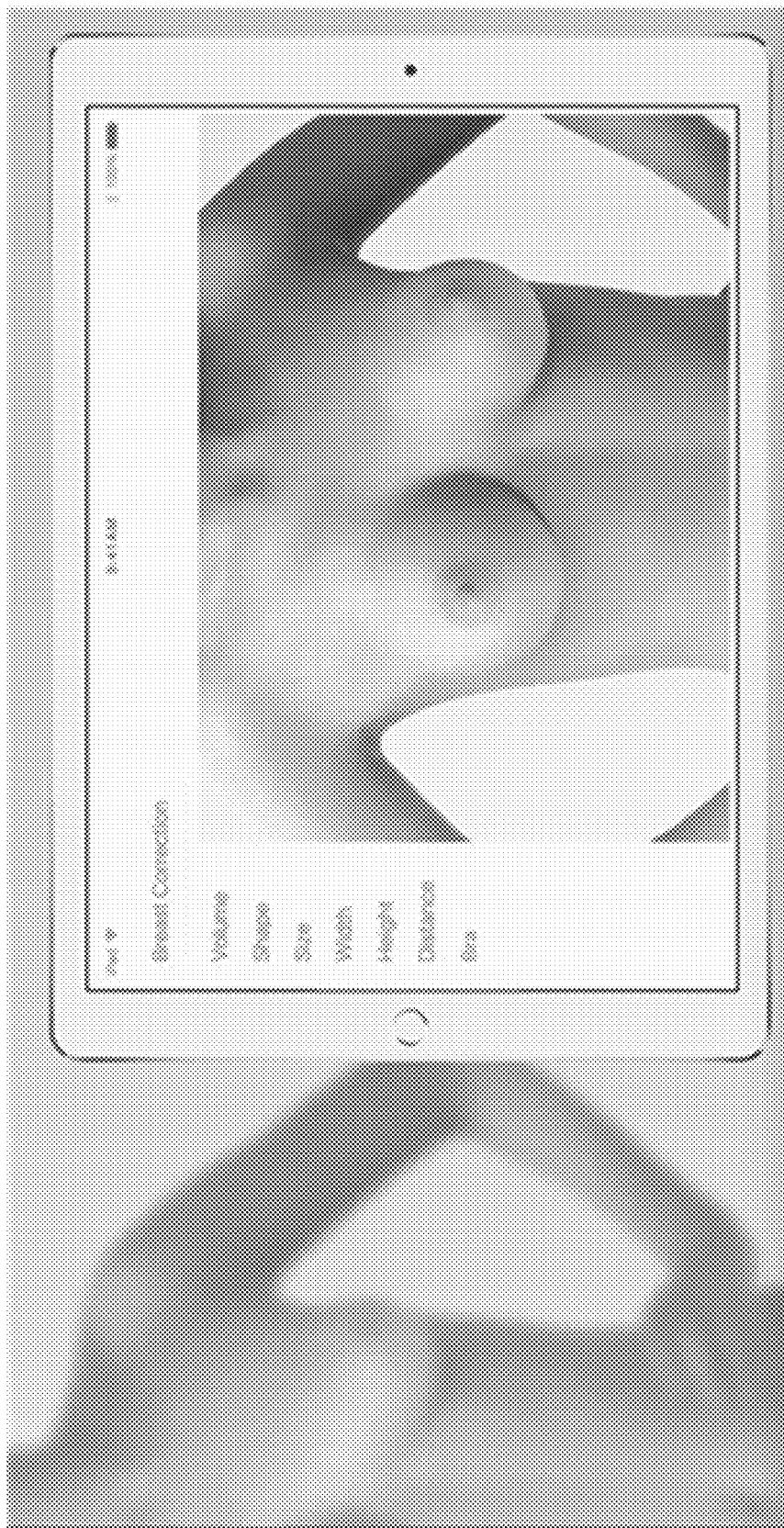
Figure 7C:
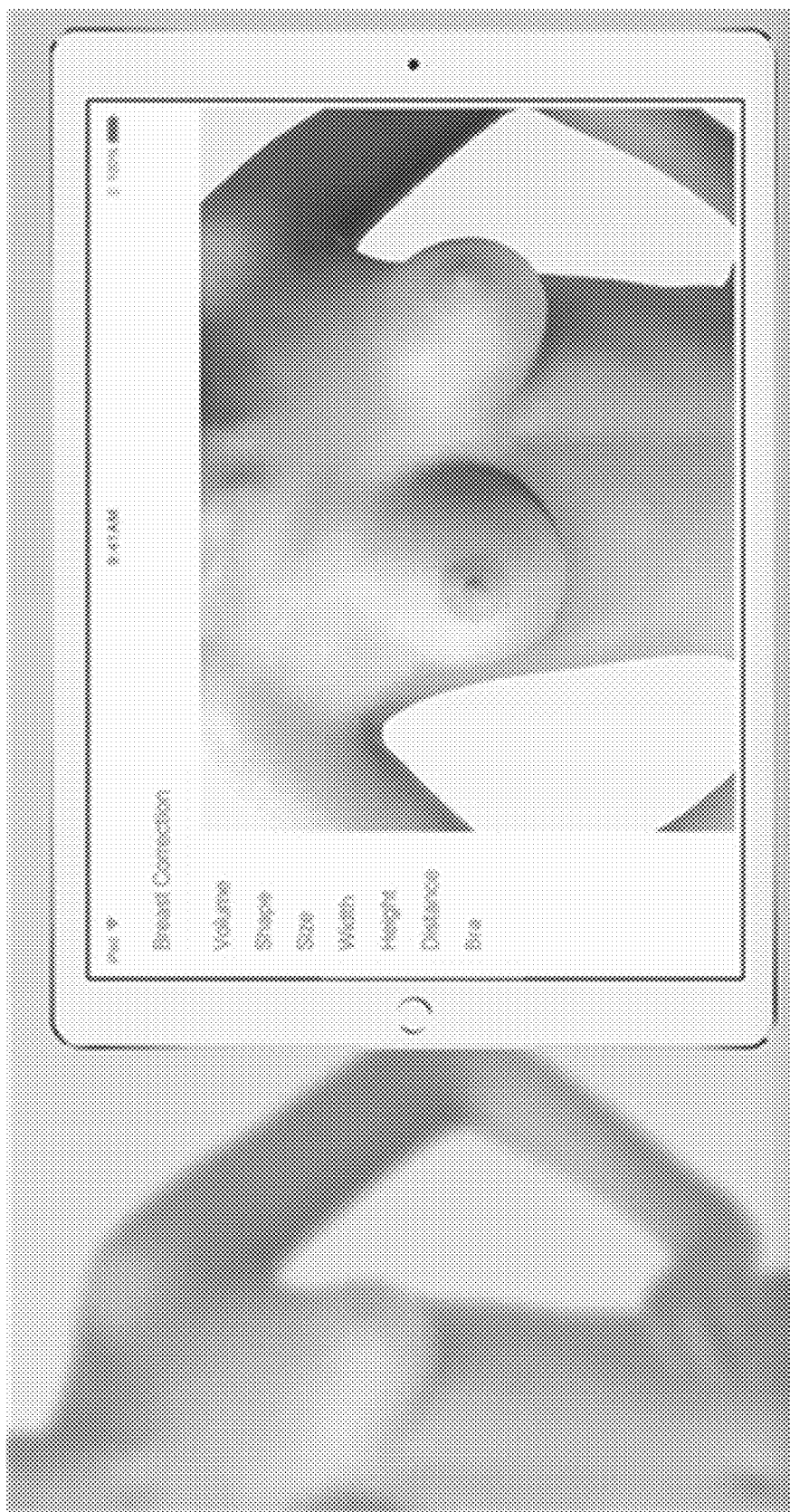

FIGS. 7A, 7B and 7C illustrate three examples of displays of virtual augmentations made to an original breast image.

Figure 8:
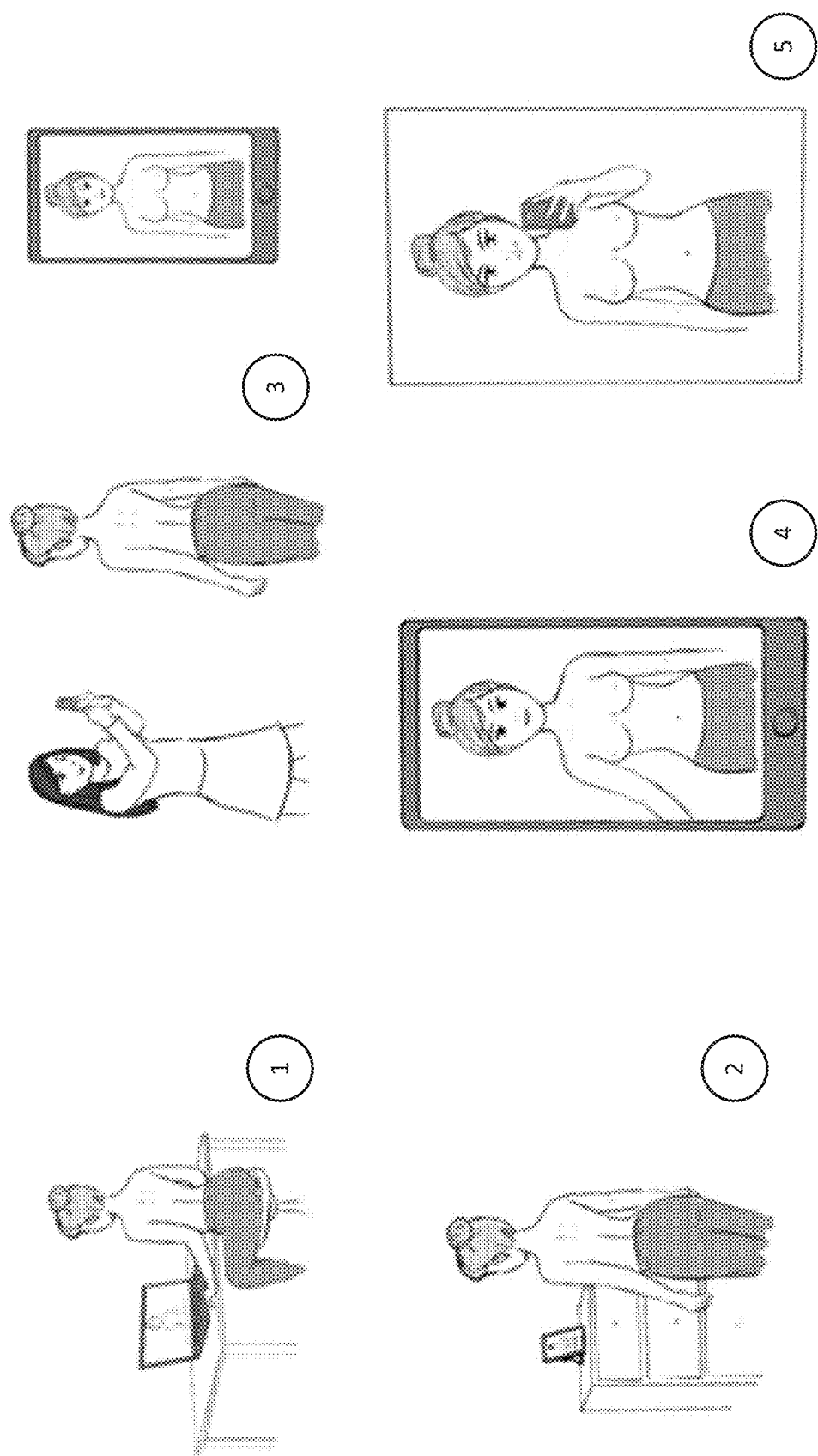
FIG. 8 illustrates steps of an image capture process showing potential scenarios, user poses and devices that could be handled and represented according to embodiments of the present invention.

FIG. 8 illustrates steps of an image capture process showing potential scenarios, user poses and devices that could be handled and represented according to embodiments of the present invention. As shown there, in step 801, a female patient positions herself in front of an image capture device such as a laptop, or a smartphone (step 802) or has another person take the picture (step 803). The patient can then see a simulated "after" image (step 804) or 805.

Figure 9:
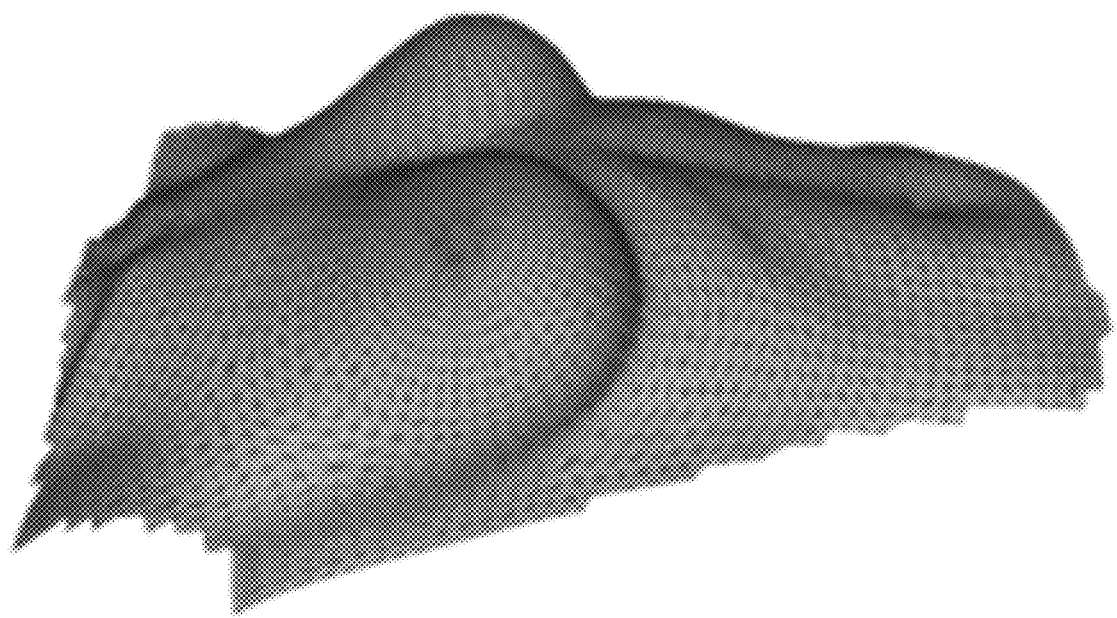
FIG. 9 illustrates a template for an upper torso mesh that might be used in 3D model generation and rendering.
Figure 9:
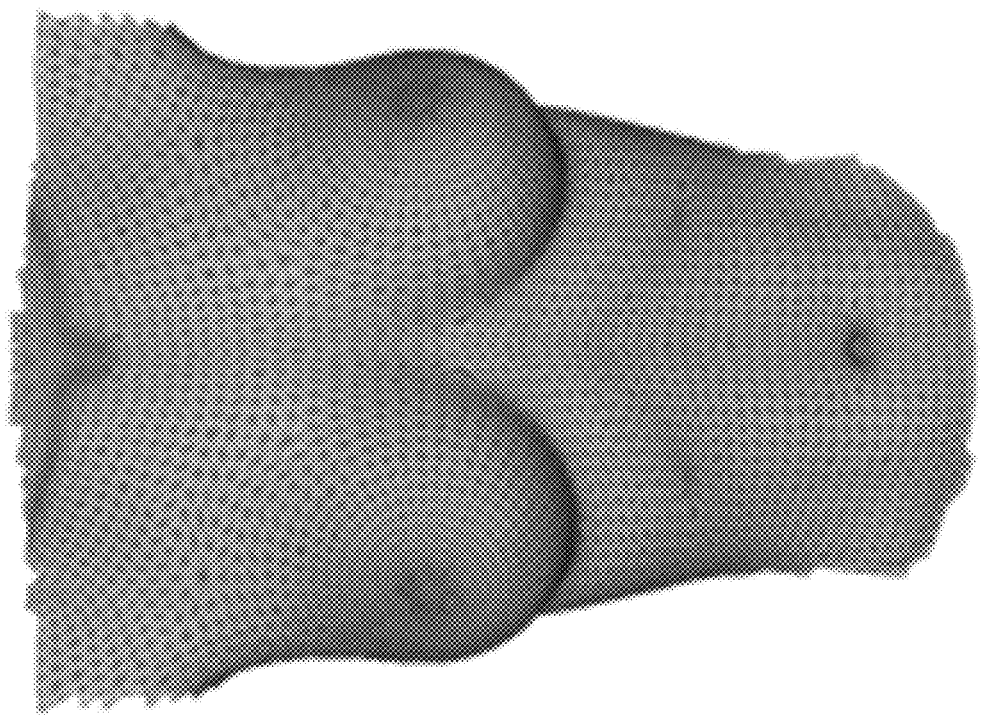

FIG. 9 illustrates a template for an upper torso mesh that might be used in 3D model generation and rendering.

The above procedure is based on machine learning, with algorithms trained on captured data along with realistically generated synthetic data, augmented by changing shapes, textures, lighting etc. In addition to Convolutional Neural Networks (CNNs) utilized for the tracking, shape fitting, the present inventions would employ techniques based on Generative Adversarial Neural Networks (GANs) and variational auto-encoders for data augmentation, mapping from low to high resolutions, image in-painting and appearance/texture enhancements.

For realism, a skin appearance model, which can be learned from real data, can be used. This can be important for real-time rendering, as it helps to sidestep skin properties necessary to be included in a rendering, e.g., subsurface scattering. Based on CNNs, the app could learn a parametric data driven skin model from a few views of the patient as she turns in front of the camera. Starting from ground truth captures, the app could learn a CNN mapping from the images to parameters of an approximate subsurface scattering light model BSSRDF, with parameters estimated by, e.g., differentiable rendering. This might require good physically based rendering, to generate realistic data. Thus, the app might prompt the patient to move relative to the camera until an image of their body is shown on a display along with guides such as lines, curves, silhouettes, etc. and the body aligns with those guides. The app may prompt the patient to press a button to indicate the alignment. In image processing, the app can assume after that process that the patient's body is at a particular position. From that, a more accurate model might be generated, perhaps including some skin texture derived from imagery of actual skin, than if the processor had to guess as to the position. From the imagery, the app can generate a data structure that represents a skin appearance model. That model can be used in rendering of the combined image that combines the patient's body with the proposed surgical simulation. With a good appearance model, the app can more easily ensure that the proposed surgical simulation portions that are overlaid on the imagery of the patient's body will remain in place relative to body movements.

A rendering may need to match aspects of the capturing camera (color gamut, noise level, focus, motion blur, etc.). Alternatively a GAN can be utilized that takes a poor render as input and produces an image that matches the camera image perfectly or nearly perfectly. A GAN can be trained to map renderings obtained from a ground truth capture (albedo, plus reconstructed mesh, plus estimated light) to the real texture itself. This generalizes to cases where the reconstructed mesh is altered, as in an "after" simulated image.

In order to potentially enhance the output images of the GANs, which might produce lower resolution than needed, the app might employ a super-resolution CNN-based method that maps low resolution images to high resolution images. An initial rendering can be obtained utilizing texture extracted from the given images to compute the parametric appearance model. This is then enhanced by passing it through the GAN architecture to improve realism.

In some embodiments, data structures are used by various components and tools, some of which are described in more detail herein. The data structures and program code used to operate on the data structures may be provided and/or carried by a transitory computer readable medium, e.g., a transmission medium such as in the form of a signal transmitted over a network.

According to some embodiments, the techniques described herein are implemented by one or more generalized computing systems programmed to perform the techniques pursuant to program instructions in firmware, memory, other storage, or a combination. Special-purpose computing devices may be used, such as desktop computer systems, portable computer systems, handheld devices, networking devices or any other device that incorporates hard-wired and/or program logic to implement the techniques.

One embodiment might include a carrier medium carrying data that includes data having been processed by the methods described herein. The carrier medium can comprise any medium suitable for carrying the data, including a storage medium, e.g., solid-state memory, an optical disk or a magnetic disk, or a transient medium, e.g., a signal carrying the data such as a signal transmitted over a network, a digital signal, a radio frequency signal, an acoustic signal, an optical signal or an electrical signal.

Figure 10:
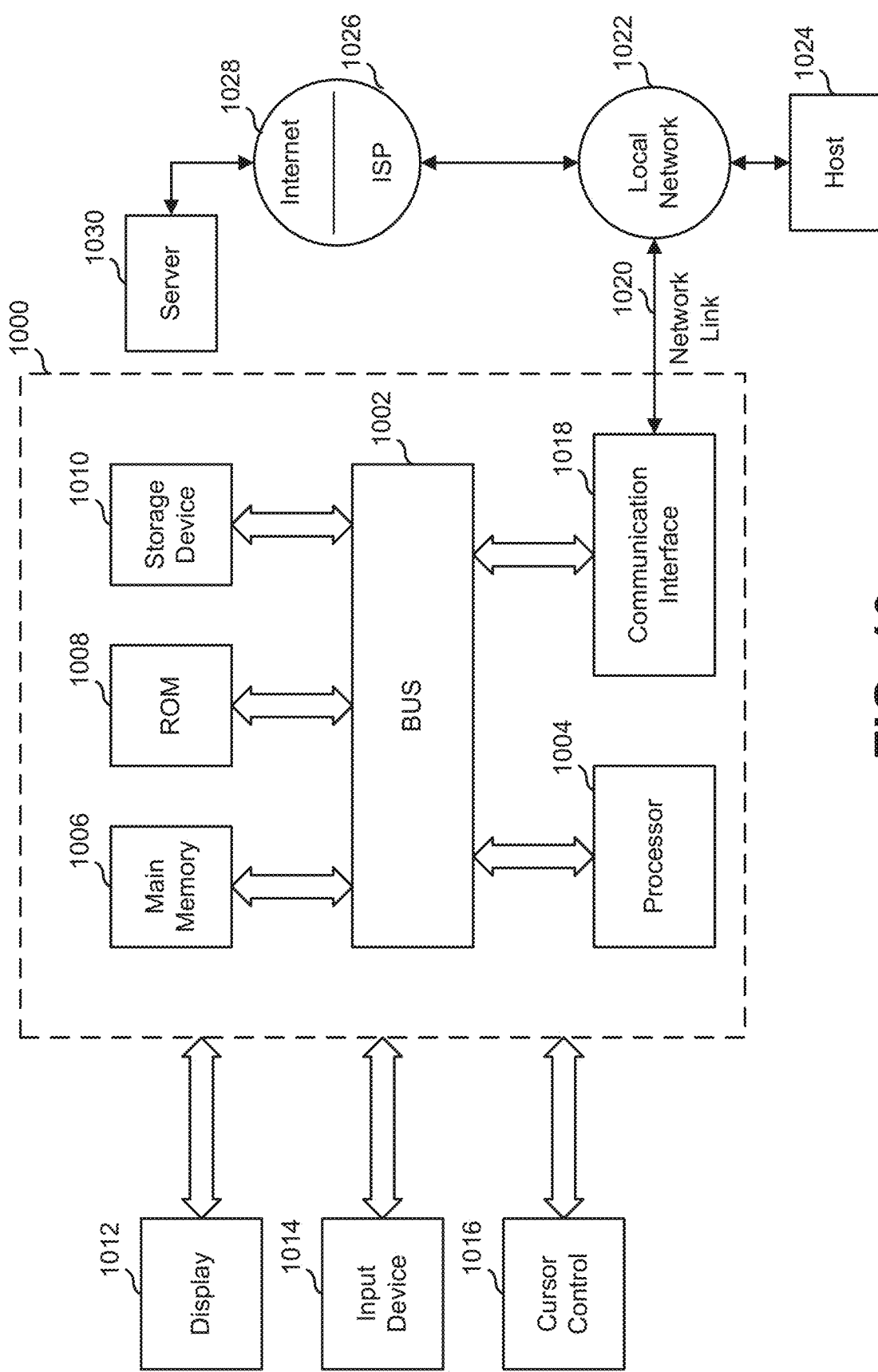
FIG. 10 is a block diagram of a computer that might be used to implement elements, features and/or functionality described herein.

FIG. 10 is a block diagram that illustrates a computer system 1000 upon which the computer systems of the systems described herein and/or data structures shown or described herein may be implemented. Computer system 1000 includes a bus 1002 or other communication mechanism for communicating information, and a processor 1004 coupled with bus 1002 for processing information. Processor 1004 may be, for example, a general-purpose microprocessor.

Computer system 1000 also includes a main memory 1006, such as a random-access memory (RAM) or other dynamic storage device, coupled to bus 1002 for storing information and instructions to be executed by processor 1004. Main memory 1006 may also be used for storing temporary variables or other intermediate information during execution of instructions to be executed by processor 1004. Such instructions, when stored in non-transitory storage media accessible to processor 1004, render computer system 1000 into a special-purpose machine that is customized to perform the operations specified in the instructions.

Computer system 1000 further includes a read only memory (ROM) 1008 or other static storage device coupled to bus 1002 for storing static information and instructions for processor 1004. A storage device 1010, such as a magnetic disk or optical disk, is provided and coupled to bus 1002 for storing information and instructions.

Computer system 1000 may be coupled via bus 1002 to a display 1012, such as a computer monitor, for displaying information to a computer user. An input device 1014, including alphanumeric and other keys, is coupled to bus 1002 for communicating information and command selections to processor 1004. Another type of user input device is a cursor control 1016, such as a mouse, a trackball, or cursor direction keys for communicating direction information and command selections to processor 1004 and for controlling cursor movement on display 1012. This input device typically has two degrees of freedom in two axes, a first axis (e.g., x) and a second axis (e.g., y), that allows the device to specify positions in a plane.

Computer system 1000 may implement the techniques described herein using customized hard-wired logic, one or more ASICs or FPGAs, firmware and/or program logic which in combination with the computer system causes or programs computer system 1000 to be a special-purpose machine. According to one embodiment, the techniques herein are performed by computer system 1000 in response to processor 1004 executing one or more sequences of one or more instructions contained in main memory 1006. Such instructions may be read into main memory 1006 from another storage medium, such as storage device 1010. Execution of the sequences of instructions contained in main memory 1006 causes processor 1004 to perform the process steps described herein. In alternative embodiments, hard-wired circuitry may be used in place of or in combination with software instructions.

The term "storage media" as used herein refers to any non-transitory media that store data and/or instructions that cause a machine to operation in a specific fashion. Such storage media may include non-volatile media and/or volatile media. Non-volatile media includes, for example, optical or magnetic disks, such as storage device 1010. Volatile media includes dynamic memory, such as main memory 1006. Common forms of storage media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, an EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire, and fiber optics, including the wires that include bus 1002. Transmission media can also take the form of acoustic or light waves, such as those generated during radio-wave and infra-red data communications.

Various forms of media may be involved in carrying one or more sequences of one or more instructions to processor 1004 for execution. For example, the instructions may initially be carried on a magnetic disk or solid-state drive of a remote computer. The remote computer can load the instructions into its dynamic memory and send the instructions over a network connection. A modem or network interface local to computer system 1000 can receive the data. Bus 1002 carries the data to main memory 1006, from which processor 1004 retrieves and executes the instructions. The instructions received by main memory 1006 may optionally be stored on storage device 1010 either before or after execution by processor 1004.

Computer system 1000 also includes a communication interface 1018 coupled to bus 1002. Communication interface 1018 provides a two-way data communication coupling to a network link 1020 that is connected to a local network 1022. For example, communication interface 1018 may be a network card, a modem, a cable modem, or a satellite modem to provide a data communication connection to a corresponding type of telephone line or communications line. Wireless links may also be implemented. In any such implementation, communication interface 1018 sends and receives electrical, electromagnetic, or optical signals that carry digital data streams representing various types of information.

Network link 1020 typically provides data communication through one or more networks to other data devices. For example, network link 1020 may provide a connection through local network 1022 to a host computer 1024 or to data equipment operated by an Internet Service Provider (ISP) 1026. ISP 1026 in turn provides data communication services through the world-wide packet data communication network now commonly referred to as the "Internet" 1028. Local network 1022 and Internet 1028 both use electrical, electromagnetic, or optical signals that carry digital data streams. The signals through the various networks and the signals on network link 1020 and through communication interface 1018, which carry the digital data to and from computer system 1000, are example forms of transmission media.

Computer system 1000 can send messages and receive data, including program code, through the network(s), network link 1020, and communication interface 1018. In the Internet example, a server 1030 might transmit a requested code for an application program through the Internet 1028, ISP 1026, local network 1022, and communication interface 1018. The received code may be executed by processor 1004 as it is received, and/or stored in storage device 1010, or other non-volatile storage for later execution.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory. The code may also be provided carried by a transitory computer readable medium e.g., a transmission medium such as in the form of a signal transmitted over a network.

Conjunctive language, such as phrases of the form "at least one of A, B, and C," or "at least one of A, B and C," unless specifically stated otherwise or otherwise clearly contradicted by context, is otherwise understood with the context as used in general to present that an item, term, etc., may be either A or B or C, or any nonempty subset of the set of A and B and C. For instance, in the illustrative example of a set having three members, the conjunctive phrases "at least one of A, B, and C" and "at least one of A, B and C" refer to any of the following sets: {A}, {B}, {C}, {A, B}, {A, C}, {B, C}, {A, B, C}. Thus, such conjunctive language is not generally intended to imply that certain embodiments require at least one of A, at least one of B and at least one of C each to be present.

The use of examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

In the foregoing specification, embodiments of the invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction.

Further embodiments can be envisioned to one of ordinary skill in the art after reading this disclosure. In other embodiments, combinations or sub-combinations of the above-disclosed invention can be advantageously made. The example arrangements of components are shown for purposes of illustration and combinations, additions, re-arrangements, and the like are contemplated in alternative embodiments of the present invention. Thus, while the invention has been described with respect to exemplary embodiments, one skilled in the art will recognize that numerous modifications are possible.

For example, the processes described herein may be implemented using hardware components, software components, and/or any combination thereof. The specification and drawings are, accordingly, to be regarded in an illustrative rather than a restrictive sense. It will, however, be evident that various modifications and changes may be made thereunto without departing from the broader spirit and scope of the invention as set forth in the claims and that the invention is intended to cover all modifications and equivalents within the scope of the following claims.

All references, including publications, patent applications, and patents, cited herein are hereby incorporated by reference to the same extent as if each reference were individually and specifically indicated to be incorporated by reference and were set forth in its entirety herein.

What is claimed is:

1. A method of generating a modified view image, of a user body part of a user, from a user input image depicting the user body part, the method comprising:

generating a first set of images comprising a first plurality of two-dimensional images from the first set of images;
generating a first set of semantic landmarks in images of the first set of images;
training a first convolutional neural network (CNN) with inputs of the first set of images with a first ground truth of the first set of semantic landmarks, wherein the training is to train the first CNN to form a first trained CNN to output one or more output semantic landmarks related to an input image without requiring a ground truth of the input image;
obtaining the user input image depicting the user body part;
generating, using the first trained CNN with the user input image as a CNN input, a second set of semantic landmarks representing landmarks of the user body part;
obtaining a mesh model for the first set of images, wherein the mesh model is a data structure that corresponds to a sampling of a three-dimensional (3D) model of instances of sampled body parts of persons other than the user;
generating, from the mesh model and the second set of semantic landmarks, a user body part mesh, wherein the user body part mesh is an approximation of a 3D model for the user body part depicted in the user input image;
obtaining a target body part mesh data structure, distinct from the user body part mesh; and
generating the modified view image of the user body part, modified to reflect differences between the target body part mesh data structure and the user body part mesh while retaining at least some texture of the user body part from the user input image.

2. The method of claim 1, wherein the target body part mesh data structure comprises a 3D post-surgery example body shape model.

3. The method of claim 1, wherein the first set of semantic landmarks in the images of the first set of images are obtained by projecting 3D vertices from sources for generating the first set of images from synthetic mesh parts onto the first set of images.

4. The method of claim 1, wherein the mesh model is generated using a silhouette contour.

5. The method of claim 1, wherein the user body part mesh is approximated using differentiable rendering.

6. The method of claim 1, further comprising displaying the modified view image, of the user body part, in an augmented reality apparatus, wherein the modified view image comprises a rendering of a 3D augmented-reality model that visually combines a first view of a first 3D model of the user body part and a second view of a second 3D model of a post-surgery example body shape, and wherein the 3D augmented-reality model includes mapping of portions of the first 3D model of the user body part to portions of the second 3D model of the post-surgery example body shape.

7. The method of claim 1, wherein generating the user body part mesh comprises generating the user body part mesh from one or more of a morphable mesh, a parametric mesh model, or a parametric model.

8. A computational device for generating a modified view image, of a body part of a present patient, comprising:
a first storage to store a first set of images comprising a first plurality of two-dimensional images from the first set of images;

a camera to capture an input image depicting the body part of the present patient; and a processor to:
  generate a first set of semantic landmarks in images of the first set of images;
  obtain a second set of images, wherein the second set of images includes instances of sampled body parts of persons other than the present patient and corresponding to a body part depicted in the input image of the present patient, wherein at least a second image of the second set of images and a third image of the second set of images have different photographic parameters;
  obtain a second set of semantic landmarks in images of the second set of images;
  train a first convolutional neural network (CNN) with inputs of the first set of images and the second set of images with a first ground truth of the first set of semantic landmarks and the second set of semantic landmarks, wherein training is to train the first CNN to form a first trained CNN to output one or more output semantic landmarks related to an input image without requiring a ground truth of the input image;
  generate, using the first trained CNN with the input image of the present patient as a CNN input, a third set of semantic landmarks representing landmarks of the body part;
  obtain a mesh model for the second set of images, wherein the mesh model corresponds to a three-dimensional (3D) instance model, of the instances of the sampled body parts of persons other than the present patient;
  generate, from the mesh model and the third set of semantic landmarks, a body part mesh, wherein the body part mesh is an approximation of a 3D model for the body part depicted in the input image;
  obtain a target body part mesh, distinct from the body part mesh; and
  generate the modified view image of the body part, modified to reflect differences between the target body part mesh and the body part mesh while retaining at least some texture of the body part from the input image of the present patient.

9. The computational device of claim 8, wherein the target body part mesh comprises a three-dimensional post-surgery example body shape model.

10. The computational device of claim 8, wherein the different photographic parameters comprise at least one of lighting conditions under which a given image was captured, albedo conditions under which the given image was captured, or camera parameters with which the given image was captured.

11. The computational device of claim 8, wherein the first set of semantic landmarks in the images of the first set of images are obtained by projecting 3D vertices from sources for generating the first set of images from synthetic mesh parts onto the first set of images, and wherein the second set of semantic landmarks in the images of the second set of images are obtained by aligning displacements of obtained landmarks that are output from the first trained CNN having as input the second set of images.

12. The computational device of claim 8, wherein the mesh model for the second set of images is generated using a silhouette contour.

13. The computational device of claim 8, wherein the body part mesh is approximated using differentiable rendering.

14. The computational device of claim 8, further comprising displaying the modified view image, of the body part, in an augmented reality apparatus, wherein the modified view image comprises a rendering of a 3D augmented-reality model that visually combines a first view of a first 3D model of the body part and a second view of a second 3D model of a post-surgery example body shape.

15. The computational device of claim 8, wherein generating the body part mesh comprises generating the body part mesh from one or more of a morphable mesh, a parametric mesh model, or a parametric model.

16. A non-transitory computer readable medium comprising instructions that, when executed by a computational device, cause the computational device to perform operations for generating a modified view image, of a user body part of a user, from a user input image depicting the user body part, the operations comprising:
  generating a first set of images comprising a first plurality of two-dimensional images from the first set of images;
  generating a first set of semantic landmarks in images of the first set of images;
  training a first convolutional neural network (CNN) with inputs of the first set of images with a first ground truth of the first set of semantic landmarks, wherein the training is to train the first CNN to form a first trained CNN to output one or more output semantic landmarks related to an input image without requiring a ground truth of the input image;
  obtaining the user input image depicting the user body part;
  generating, using the first trained CNN with the user input image as a CNN input, a second set of semantic landmarks representing landmarks of the user body part;
  obtaining a mesh model for the first set of images, wherein the mesh model is a data structure that corresponds to a sampling of a three-dimensional (3D) model of instances of sampled body parts of persons other than the user;
  generating, from the mesh model and the second set of semantic landmarks, a user body part mesh, wherein the user body part mesh is an approximation of a 3D model for the user body part depicted in the user input image;
  obtaining a target body part mesh data structure, distinct from the user body part mesh; and
  generating the modified view image of the user body part, modified to reflect differences between the target body part mesh data structure and the user body part mesh while retaining at least some texture of the user body part from the user input image.

17. The non-transitory computer readable medium of claim 16, wherein the target body part mesh data structure comprises a three-dimensional post-surgery example body shape model.

18. The non-transitory computer readable medium of claim 16, wherein the first set of semantic landmarks in the images of the first set of images are obtained by projecting 3D vertices from sources for generating the first set of images from synthetic mesh parts onto the first set of images.

19. The non-transitory computer readable medium of claim 16, wherein the mesh model is generated using a silhouette contour.

20. The non-transitory computer readable medium of claim 16, wherein the user body part mesh is approximated using differentiable rendering.

21. The non-transitory computer readable medium of claim 16, the operations further comprising:
   displaying the modified view image, of the user body part, in an augmented reality apparatus, wherein the modified view image comprises a rendering of a 3D augmented-reality model that visually combines a first view of a first 3D model of the user body part and a second view of a second 3D model of a post-surgery example body shape, and wherein the 3D augmented-reality model includes mapping of portions of the first 3D model of the user body part to portions of the second 3D model of the post-surgery example body shape.

22. The non-transitory computer readable medium of claim 16, wherein generating the user body part mesh comprises generating the user body part mesh from one or more of a morphable mesh, a parametric mesh model, or a parametric model.

\* \* \* \* \*